United States Patent
Kohara et al.

(10) Patent No.: US 6,849,753 B2
(45) Date of Patent: Feb. 1, 2005

(54) PROCESS FOR PREPARATION OF HALF-VANADOCENE COMPOUND

(75) Inventors: Tadanao Kohara, Anan (JP); Tomoya Kubo, Anan (JP)

(73) Assignee: Nichia Corporation, Tokushima (JP)

( * ) Notice: Subject to any disclaimer, the term of this patent is extended or adjusted under 35 U.S.C. 154(b) by 81 days.

(21) Appl. No.: 10/298,624

(22) Filed: Nov. 15, 2002

(65) Prior Publication Data

US 2003/0109733 A1 Jun. 12, 2003

(30) Foreign Application Priority Data

Nov. 19, 2001 (JP) ........................................ 2001-353836

(51) Int. Cl.$^7$ .......................... C07F 17/00; B01J 31/00; C08F 4/44
(52) U.S. Cl. .......................... 556/43; 502/103; 502/117; 526/160; 526/943
(58) Field of Search .......................... 556/43; 502/103, 502/117; 526/160, 943

(56) References Cited

U.S. PATENT DOCUMENTS

| | | | | |
|---|---|---|---|---|
| 2,882,288 A | * | 4/1959 | Brantley et al. | 556/43 |
| 3,080,305 A | * | 3/1963 | Gorsich | 204/157.75 |

FOREIGN PATENT DOCUMENTS

| | | |
|---|---|---|
| DE | 198 32 442 | 7/1998 |
| EP | 0 778 291 | 6/1997 |
| JP | 10-218934 | 8/1998 |
| JP | 10-298191 | 11/1998 |
| JP | 10-298230 | 11/1998 |
| JP | 10-306116 | 11/1998 |
| JP | 11-130779 | 5/1999 |

OTHER PUBLICATIONS

Journal of Organometallic Chemistry; 319, C21–C24 1987.
Z. Naturforsch "Oxochlorination of Transition Metal Complexes with Thionyl Chloride," pp. 153–156 1998.
Tr.Khim.Khim.Tekhnol, "Reaction of vanadocene with tert-butylhydroperoxide and tert-butylper benzoate," 4 , pp.32–34 1974.
K.H. Thiele, et al., "Contributions to the Chemistry of Transition Metal Alkyl Compounds, XIX. On the Preparation and Properties of Cyclopentadienyl Vanadium Trichloride," Z.Anorg. Allg. Chem. 423, pp.231–234 1976.

* cited by examiner

*Primary Examiner*—Porfirio Nazario-Gonzalez
(74) *Attorney, Agent, or Firm*—Knobbe, Martens, Olson & Bear, LLP.

(57) ABSTRACT

A process for preparing a half-vanadocene compound, the process comprising reacting chlorine gas with a vanadocene compound represented by the formula (1)

$$Cp_2VX_2 \quad (1)$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl, and the two Cp groups may be the same or different, X represents fluorine, chlorine, bromine or iodine and the two X atoms may be the same or different.

7 Claims, No Drawings

PROCESS FOR PREPARATION OF HALF-VANADOCENE COMPOUND

BACKGROUND OF THE INVENTION

1. Field of the Invention

The present invention relates to a process for preparing a half-vanadocene compound and more particularly to a process for preparing a half-vanadocene compound in a high yield using a chemically stable vanadocene compound as a starting material.

2. Description of Related Art

A half-vanadocene compound, typically vanadium complex of cyclopentadiene, is widely used as a catalyst for polymerization of olefins or diolefins. The half-vanadocene compound exhibits a high activity as a catalyst for polymerization of butadiene, and is an important catalyst which is indispensable in organic synthesis.

Examples of the half-vanadocene compound include $(C_5H_5)VOCl_2$, $(C_5H_5)VCl_3$ and the like. A number of processes are known for preparing such half-vanadocene compounds.

It was reported to prepare $(C_5H_5)VOCl_2$ by reacting $(C_5H_5)V(CO)_4$ with a mixed gas of oxygen and chlorine (J. Organomet. Chem., No. 319, page C21 (1987)). Further reported was a process for preparing $(C_5H_5)VOCl_2$ by reacting $(C_5H_5)V(CO)_4$ with oxygen and $SOCl_2$ (Z. Naturforsch., B: Chem. Sci., No. 53, p. 153 (1998)).

However, these processes pose problems. If purified $(C_5H_5)V(CO)_4$ is not used as the starting material, the contemplated compound can not be produced with a high purity in a high yield. Further these processes are not practical in other respects. $(C_5H_5)V(CO)_4$ used as the starting material is likely to decompose, and a large amount of toxic carbon monoxide is required in preparation of the compound. Moreover, a large amount of toxic carbon monoxide is produced in chlorination of $(C_5H_5)V(CO)_4$.

A process was reported for preparing $(C_5H_5)VOCl_2$ by reacting $(C_5H_5)_2V$ with $(CH_3)_3COOH$ to give $(C_5H_5)VO_2$ and treating the obtained compound with $SOCl_2$. (Tr. Khim. Khim. Tekhnol., Vol. 4, p. 32 (1974)). This process necessitates separation and removal of by-products in the cause of the reaction so that the reaction involves a prolonged reaction procedure for conversion of an industrial raw material $VCl_4$ to $(C_5H_5)VOCl_2$. Thus the process is not practical.

Japanese Unexamined Patent Publications No. 298191/1998 and No. 130779/1999 disclose processes for preparing $(C_5H_5)VOCl_2$ by reacting $VOCl_3$ with $(C_5H_5)MgCl$. However, the $(C_5H_5)VOCl_2$ is produced in a yield of as low as 25%. Thus the disclosed processes are not practical.

Also reported was a process for preparing $(C_5H_5)VCl_3$ which comprises reacting $(C_5H_5)V(CO)_4$ with $SOCl_2$ (Z. Anorg. Allg. Chem., No. 423, p. 231 (1976)). This process needs $(C_5H_5)V(CO)_4$ as the raw material and is not practical.

The above-mentioned publication also discloses a process for preparing $(C_5H_5)VCl_3$ which comprises treating $(C_5H_5)_2VCl_2$ with $SOCl_2$. However, when purified $(C_5H_5)_2VCl_2$ is not used as the raw material, a high-purity $(C_5H_5)VCl_3$ would not be produced in a high yield.

As described above, prior art processes for preparing a half-vanadocene compound are not practical in that the starting compound is likely to decompose and a half-vanadocene compound can not be produced in a sufficiently high yield.

BRIEF SUMMARY OF THE INVENTION

An object of the present invention is to provide a process for easily preparing a half-vanadocene compound with a high purity.

The present inventor carried out research to achieve the foregoing object and found that a half-vanadocene compound can be produced with a high purity in a high yield by reacting chlorine gas with a vanadocene compound represented by the formula (1)

$$Cp_2VX_2 \tag{1}$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl, and the two Cp groups may be the same or different, X represents fluorine, chlorine, bromine or iodine, and the two X atoms may be the same or different.

The present invention was completed based on the foregoing novel finding and provides the following processes for preparing a half-vanadocene compound:

1. A process for preparing a half-vanadocene compound, the process comprising reacting chlorine gas with a vanadocene compound represented by the formula (1)

$$Cp_2VX_2 \tag{1}$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl, and the two Cp groups may be the same or different, X represents fluorine, chlorine, bromine or iodine and the two X atoms may be the same or different, either in the presence of at least one member selected from group consisting of oxygen and water or in the absence of oxygen and water.

2. A process for preparing a half-vanadocene compound according to item 1, wherein Cp represents cyclopentadienyl; cyclopentadienyl having 1 to 5 substituents selected from the group consisting of hydrocarbon groups having 1 to 20 carbon atoms and silicon-containing hydrocarbon groups having 1 to 20 carbon atoms; indenyl; indenyl having 1 to 6 substituents selected from the group consisting of hydrocarbon groups having 1 to 20 carbon atoms and silicon-containing hydrocarbon groups having 1 to 20 carbon atoms; fluorenyl; fluorenyl having 1 to 8 substituents selected from the group consisting of hydrocarbon groups having 1 to 20 carbon atoms and silicon-containing hydrocarbon groups having 1 to 20 carbon atoms; benzoindenyl; benzoindenyl having 1 to 8 substituents selected from the group consisting of hydrocarbon groups having 1 to 20 carbon atoms and silicon-containing hydrocarbon groups having 1 to 20 carbon atoms; azulenyl; or azulenyl having 1 to 7 substituents selected from the group consisting of hydrocarbon groups having 1 to 20 carbon atoms and silicon-containing hydrocarbon groups having 1 to 20 carbon atoms, and the two Cp groups may be the same or different.

3. A process for preparing a half-vanadocene compound according to item 1 or 2, wherein Cp represents cyclopentadienyl; cyclopentadienyl having 1 to 5 substituents selected from the group consisting of methyl, ethyl, n-propyl, iso-propyl, n-butyl, iso-butyl, sec-butyl, t-butyl and phenyl; indenyl; indenyl having 1 to 6 substituents selected from the group consisting of methyl, ethyl, n-propyl, iso-propyl, n-butyl, iso-butyl, sec-butyl, t-butyl and phenyl; fluorenyl; fluorenyl having 1 to 8 substituents selected from the group consisting of methyl, ethyl, n-propyl, iso-propyl, n-butyl, iso-butyl, sec-butyl, t-butyl and phenyl; benzoindenyl; benzoindenyl having 1 to 8 substituents selected from the group consisting of methyl, ethyl, n-propyl, iso-propyl, n-butyl, iso-butyl, sec-butyl, t-butyl and phenyl; azulenyl; or azulenyl having 1 to 7 substituents selected from the group consisting of methyl, ethyl, n-propyl, iso-propyl, n-butyl, iso-butyl, sec-butyl, t-butyl and phenyl, and the two Cp groups may be the same or different.

4. The process for preparing a half-vanadocene compound according to item 1, 2 or 3, wherein the compound represented by the formula (1) is selected from the group consisting of $(C_5H_5)_2VF_2$, $(C_5H_5)_2VCl_2$, $(C_5H_5)_2VBr_2$, $(C_5H_5)_2VI_2$, $(CH_3C_5H_4)_2VF_2$, $(CH_3C_5H_4)_2VCl_2$, $(CH_3C_5H_4)_2VBr_2$, $(CH_3C_5H_4)_2VI_2$, $[1,2-(CH_3)_2C_5H_3]_2VF_2$, $[1,2-(CH_3)_2C_5H_3]_2VCl_2$, $[1,2-(CH_3)_2C_5H_3]_2VBr_2$, $[1,2-(CH_3)_2C_5H_3]_2VI_2$, $[1,3-(CH_3)_2C_5H_3]_2VF_2$, $[1,3-(CH_3)_2C_5H_3]_2VCl_2$, $[1,3-(CH_3)_2C_5H_3]_2VBr_2$, $[1,3-(CH_3)_2C_5H_3]_2VI_2$, $[1,2,3-(CH_3)_3C_5H_2]_2VF_2$, $[1,2,3-(CH_3)_3C_5H_2]_2VCl_2$, $[1,2,3-(CH_3)_3C_5H_2]_2VBr_2$, $[1,2,3-(CH_3)_3C_5H_2]_2VI_2$, $[1,2,4-(CH_3)_3C_5H_2]_2VF_2$, $[1,2,4-(CH_3)_3C_5H_2]_2VCl_2$, $[1,2,4-(CH_3)_3C_5H_2]_2VBr_2$, $[1,2,4-(CH_3)_3C_5H_2]_2VI_2$, $[(CH_3)_4C_5H]_2VF_2$, $[(CH_3)_4C_5H]_2VCl_2$, $[(CH_3)_4C_5H]_2VBr_2$, $[(CH_3)_4C_5H]_2VI_2$, $[(CH_3)_5C_5]_2VF_2$, $[(CH_3)_5C_5]_2VCl_2$, $[(CH_3)_5C_5]_2VBr_2$, $[(CH_3)_5C_5]_2VI_2$, $(1-CH_3-2-C_2H_5C_5H_3)_2VF_2$, $(1-CH_3-2-C_2H_5C_5H_3)_2VCl_2$, $(1-CH_3-2-C_2H_5C_5H_3)_2VBr_2$, $(1-CH_3-2-C_2H_5C_5H_3)_2VI_2$, $(1-CH_3-3-C_2H_5C_5H_3)_2VF_2$, $(1-CH_3-3-C_2H_5C_5H_3)_2VCl_2$, $(1-CH_3-3-C_2H_5C_5H_3)_2VBR_2$, $(1-CH_3-3-C_2H_5C_5H_3)_2VI_2$, $(1-CH_3-2-n-C_3H_7C_5H_3)_2VF_2$, $(1-CH_3-2-n-C_3H_7C_5H_3)_2VCl_2$, $(1-CH_3-2-n-C_3H_7C_5H_3)_2VBr_2$, $(1-CH_3-2-n-C_3H_7C_5H_3)_2VI_2$, $(1-CH_3-2-iso-C_3H_7C_5H_3)_2VF_2$, $(1-CH_3-2-iso-C_3H_7C_5H_3)_2VCl_2$, $(1-CH_3-2-iso-C_3H_7C_5H_3)_2VBr_2$, $(1-CH_3-2-iso-C_3H_7C_5H_3)_2VI_2$, $(1-CH_3-3-n-C_3H_7C_5H_3)_2VF_2$, $(1-CH_3-3-n-C_3H_7C_5H_3)_2VCl_2$, $(1-CH_3-3-n-C_3H_7C_5H_3)_2VBr_2$, $(1-CH_3-3-n-C_3H_7C_5H_3)_2VI_2$, $(1-CH_3-3-iso-C_3H_7C_5H_3)_2VF_2$, $(1-CH_3-3-iso-C_3H_7C_5H_3)_2VCl_2$, $(1-CH_3-3-iso-C_3H_7C_5H_3)_2VBr_2$, $(1-CH_3-3-iso-C_3H_7C_5H_3)_2VI_2$, $(C_2H_5C_5H_4)_2VF_2$, $(C_2H_5C_5H_4)_2VCl_2$, $(C_2H_5C_5H_4)_2VBr_2$, $(C_2H_5C_5H_4)_2VI_2$, $[1,2-(C_2H_5)_2C_5H_3]_2VF_2$, $[1,2-(C_2H_5)_2C_5H_3]_2VCl_2$, $[1,2-(C_2H_5)_2C_5H_3]_2VBr_2$, $[1,2-(C_2H_5)_2C_5H_3]_2VI_2$, $[1,3-(C_2H_5)_2C_5H_3]_2VF_2$, $[1,3-(C_2H_5)_2C_5H_3]_2VCl_2$, $[1,3-(C_2H_5)_2C_5H_3]_2VBr_2$, $[1,3-(C_2H_5)_2C_5H_3]_2VI_2$, $[1,2-(n-C_3H_7)_2C_5H_3]_2VF_2$, $[1,2-(n-C_3H_7)_2C_5H_3]_2VCl_2$, $[1,2-(n-C_3H_7)_2C_5H_3]_2VBr_2$, $[1,2-(n-C_3H_7)_2C_5H_3]_2VI_2$, $[1,3-(n-C_3H_7)_2C_5H_3]_2VF_2$, $[1,3-(n-C_3H_7)_2C_5H_3]_2VCl_2$, $[1,3-(n-C_3H_7)_2C_5H_3]_2VBr_2$, $[1,3-(n-C_3H_7)_2C_5H_3]_2VI_2$, $[1,2-(iso-C_3H_7)_2C_5H_3]_2VF_2$, $[1,2-(iso-C_3H_7)_2C_5H_3]_2VCl_2$, $[1,2-(iso-C_3H_7)_2C_5H_3]_2VBr_2$, $[1,2-(iso-C_3H_7)_2C_5H_3]_2VI_2$, $[1,3-(iso-C_3H_7)_2C_5H_3]_2VF_2$, $[1,3-(iso-C_3H_7)_2C_5H_3]_2VCl_2$, $[1,3-(iso-C_3H_7)_2C_5H_3]_2VBr_2$, $[1,3-(iso-C_3H_7)_2C_5H_3]_2VI_2$, $[1,2-(n-C_4H_9)_2C_5H_3]_2VF_2$, $[1,2-(n-C_4H_9)_2C_5H_3]_2VCl_2$, $[1,2-(n-C_4H_9)_2C_5H_3]_2VBr_2$, $[1,2-(n-C_4H_9)_2C_5H_3]_2VI_2$, $[1,3-(n-C_4H_9)_2C_5H_3]_2VF_2$, $[1,3-(n-C_4H_9)_2C_5H_3]_2VCl_2$, $[1,3-(n-C_4H_9)_2C_5H_3]_2VBr_2$, $[1,3-(n-C_4H_9)_2C_5H_3]_2VI_2$, $[1,3-(t-C_4H_9)_2C_5H_3]_2VF_2$, $[1,3-(t-C_4H_9)_2C_5H_3]_2VCl_2$, $[1,3-(t-C_4H_9)_2C_5H_3]_2VBr_2$, $[1,3-(t-C_4H_9)_2C_5H_3]_2VI_2$, $(n-C_5H_{11}C_5H_4)_2VF_2$, $(n-C_5H_{11}C_5H_4)_2VCl_2$, $(n-C_5H_{11}C_5H_4)_2VBr_2$, $(n-C_5H_{11}C_5H_4)_2VI_2$, $(n-C_6H_{13}C_5H_4)_2VF_2$, $(n-C_6H_{13}C_5H_4)_2VCl_2$, $(n-C_6H_{13}C_5H_4)_2VBr_2$, $(n-C_6H_{13}C_5H_4)_2VI_2$, $(n-C_8H_{17}C_5H_4)_2VF_2$, $(n-C_8H_{17}C_5H_4)_2VCl_2$, $(n-C_8H_{17}C_5H_4)_2VBr_2$, $(n-C_8H_{17}C_5H_4)_2VI_2$, $(C_6H_5C_5H_4)_2VF_2$, $(C_6H_5C_5H_4)_2VCl_2$, $(C_6H_5C_5H_4)_2VBr_2$, $(C_6H_5C_5H_4)_2VI_2$, $(C_6H_5CH_2C_5H_4)_2VF_2$, $(C_6H_5CH_2C_5H_4)_2VCl_2$, $(C_6H_5CH_2C_5H_4)_2VBr_2$, $(C_6H_5CH_2C_5H_4)_2VI_2$, $[(CH_3)_3SiC_5H_4]_2VF_2$, $[(CH_3)_3SiC_5H_4]_2VCl_2$, $[(CH_3)_3SiC_5H_4]_2VBr_2$, $[(CH_3)_3SiC_5H_4]_2VI_2$, $\{1,3-[(CH_3)_3Si]_2C_5H_3\}_2VF_2$, $\{1,3-[(CH_3)_3Si]_2C_5H_3\}_2VCl_2$, $\{1,3-[(CH_3)_3Si]_2C_5H_3\}_2VBr_2$, $\{1,3-[(CH_3)_3Si]_2C_5H_3\}_2VI_2$, $[(CH_3)_3Si(CH_3)C_5H_3]_2VF_2$, $[1-(CH_3)_3Si-3-CH_3C_5H_3]_2VCl_2$, $[1-(CH_3)_3Si-3-CH_3C_5H_3]_2VBr_2$, $[1-(CH_3)_3Si-3-CH_3C_5H_3]_2VI_2$, $\{1,3-[(CH_3)_3Si]_2-4-CH_3C_5H_2\}_2VF_2$, $\{1,3-[(CH_3)_3Si]_2-4-CH_3C_5H_2\}_2VCl_2$, $\{1,3-[(CH_3)_3Si]_2-4-CH_3C_5H_2\}_2VBr_2$, $\{1,3-[(CH_3)_3Si]_2-4-CH_3C_5H_2\}_2VI_2$, $Ind_2VF_2$, $Ind_2VCl_2$, $Ind_2VBr_2$, $Ind_2VI_2$, $(2-CH_3Ind)_2VF_2$, $(2-CH_3Ind)_2VCl_2$, $(2-CH_3Ind)_2VBr_2$, $(2-CH_3Ind)_2VI_2$, $(2-C_2H_5Ind)_2VF_2$, $(2-C_2H_5Ind)_2VCl_2$, $(2-C_2H_5Ind)_2VBrF_2$, $(2-C_2H_5Ind)_2VI_2$, $(2-n-C_3H_7Ind)_2VF_2$, $(2-n-C_3H_7Ind)_2VCl_2$, $(2-n-C_3H_7Ind)_2VBr_2$, $(2-n-C_3H_7Ind)_2VI_2$, $(2-iso-C_3H_7Ind)_2VF_2$, $(2-iso-C_3H_7Ind)_2VCl_2$, $(2-iso-C_3H_7Ind)_2VBr_2$, $(2-iso-C_3H_7Ind)_2VI_2$, $(2-n-C_4H_9Ind)_2VF_2$, $(2-n-C_4H_9Ind)_2VCl_2$, $(2-n-C_4H_9Ind)_2VBr_2$, $(2-n-C_4H_9Ind)_2VI_2$, $(2-t-C_4H_9Ind)_2VF_2$, $(2-t-C_4H_9Ind)_2VCl_2$, $(2-t-C_4H_9Ind)_2VBr_2$, $(2-t-C_4H_9Ind)_2VI_2$, $[2-(CH_3)_3SiInd)]_2VF_2$, $[2-(CH_3)_3SiInd)]_2VCl_2$, $[2-(CH_3)_3SiInd)]_2VBr_2$, $[2-(CH_3)_3SiInd)]_2VI_2$, $[2,4-(CH_3)_2Ind)]_2VF_2$, $[2,4-(CH_3)_2Ind)]_2VCl_2$, $[2,4-(CH_3)_2Ind)]_2VBr_2$, $[2,4-(CH_3)_2Ind)]_2VI_2$, $(2-CH_3-4-C_6H_5Ind)_2VF_2$, $(2-CH_3-4-C_6H_5Ind)_2VCl_2$, $(2-CH_3-4-C_6H_5Ind)_2VBr_2$, $(2-CH_3-4-C_6H_5Ind)_2VI_2$, $(H_4Ind)_2VF_2$, $(H_4Ind)_2VCl_2$, $(H_4Ind)_2VBr_2$, $(H_4Ind)_2VI_2$, $Flu_2VF_2$, $Flu_2VCl_2$, $Flu_2VBr_2$, $Flu_2VI_2$, $(9-CH_3Flu)_2VF_2$, $(9-CH_3Flu)_2VCl_2$, $(9-CH_3Flu)_2VBr_2$, $(9-CH_3Flu)_2VI_2$, $(9-C_2H_5Flu)_2VF_2$, $(9-C_2H_5Flu)_2VCl_2$, $(9-C_2H_5Flu)_2VBr_2$, $(9-C_2H_5Flu)_2VCl_2$, $(9-n-C_3H_7Flu)_2VF_2$, $(9-n-C_3H_7Flu)_2VCl_2$, $(9-n-C_3H_7Flu)_2VBr_2$, $(9-n-C_3H_7Flu)_2VI_2$, $(9-iso-C_3H_7Flu)_2VF_2$, $(9-iso-C_3H_7Flu)_2VCl_2$, $(9-iso-C_3H_7Flu)_2VBr_2$, $(9-iso-C_3H_7Flu)_2VI_2$, $(9-n-C_4H_9Flu)_2VF_2$, $(9-n-C_4H_9Flu)_2VCl_2$, $(9-n-C_4H_9Flu)_2VBr_2$, $(9-n-C_4H_9Flu)_2VI_2$, $[1,9-(CH_3)_2Flu]_2VF_2$, $[1,9-(CH_3)_2Flu]_2VCl_2$, $[1,9-(CH_3)_2Flu]_2VBr_2$, $[1,9-(CH_3)_2Flu]_2VI_2$, $(H_8Flu)_2VF_2$, $(H_8Flu)_2VCl_2$, $(H_8Flu)_2VBr_2$, $(H_8Flu)_2VI_2$, $Bind_2VF_2$, $Bind2VCl_2$, $Bind_2VBr_2$, $Bind_2VI_2$, $(2-CH_3Bind)_2VF_2$, $(2-CH_3Bind)_2VCl_2$, $(2-CH_3Bind)_2VBr_2$, $(2-CH_3Bind)_2VI_2$, $(2-C_2H_5Bind)_2VF_2$, $(2-C_2H_5Bind)_2VCl_2$, $(2-C_2H_5Bind)_2VBr_2$, $(2-C_2H_5Bind)_2VI_2$, $(2-n-C_3H_7Bind)_2VF_2$, $(2-n-C_3H_7Bind)_2VCl_2$, $(2-n-C_3H_7Bind)_2VBr_2$, $(2-n-C_3H_7Bind)_2VI_2$, $(2-iso-C_3H_7Bind)_2VF_2$, $(2-iso-C_3H_7Bind)_2VCl_2$, $(2-iso-C_3H_7Bind)_2VBr_2$, $(2-iso-C_3H_7Bind)_2VI_2$, $(2-n-C_4H_9Bind)_2VF_2$, $(2-n-C_4H_9Bind)_2VCl_2$, $(2-n-C_4H_9Bind)_2VBr_2$, $(2-n-C_4H_9Bind)_2VI_2$, $(2-t-C_4H_9Bind)_2VF_2$, $(2-t-C_4H_9Bind)_2VCl_2$, $(2-t-C_4H_9Bind)_2VBr_2$, $(2-t-C_4H_9Bind)_2VI_2$, $Azu_2VF_2$, $Azu2VCl_2$, $Azu_2VBr_2$, $Azu_2VI_2$, $(2-CH_3Azu)_2VF_2$, $(2-CH_3Azu)_2VCl_2$, $(2-CH_3Azu)_2VBr_2$, $(2-CH_3Azu)_2VI_2$, $(2-C_2H_5Azu)_2VF_2$, $(2-C_2H_5Azu)_2VCl_2$, $(2-C_2H_5Azu)_2VBr_2$, $(2-C_2H_5Azu)_2VI_2$, $(2-n-C_3H_7Azu)_2VF_2$, $(2-n-C_3H_7Azu)_2VCl_2$, $(2-n-C_3H_7Azu)_2VBr_2$, $(2-n-C_3H_7AZU)_2VI_2$, $(2-iso-C_3H_7Azu)_2VF_2$, $(2-iso-C_3H_7Azu)_2VCl_2$, $(2-iso-C_3H_7Azu)_2VBr_2$, $(2-iso-C_3H_7Azu)_{2VI2}$, $(4,8-(CH_3)_2Azu)_2VF_2$, $(4,8-(CH_3)_2Azu)_2VCl_2$, $(4,8-(CH_3)_2Azu)_2VBr_2$, $(4,8-(CH_3)_2Azu)_2VI_2$, $(2,4,8-(CH_3)_3Azu)_2VF_2$, $(2,4,8-(CH_3)_3Azu)_2VCl_2$, $(2,4,8-(CH_3)_3Azu)_2VBr_2$, $(2,4,8-(CH_3)_3Azu)_2VI_2$, $[2-iso-C_3H_7-4,8-(CH_3)_2Azu]_2VF_2$, $[2-iso- $C_3H_7$-4,8-$(CH_3)_2$Azu]$_2$VCl$_2$, [2-iso-$C_3H_7$-4,8-$(CH_3)_2$Azu]$_2$VBr$_2$ and [2-iso-$C_3H_7$-4,8-$(CH_3)_2$Azu]$_2$VI$_2$, wherein Ind represents indenyl, Flu represents fluorenyl, Bind represents benzoindenyl, Azu represents azulenyl, $H_4$Ind represents the following group (6),

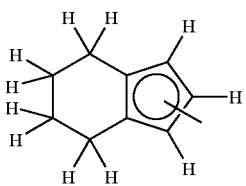

(6)

and $H_8$Flu represents the following group (7).

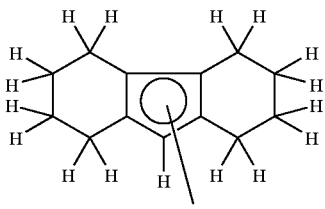

(7)

5. The process for preparing a half-vanadocene compound according to any of items 1 to 4, wherein the vanadocene compound represented by the formula (1) is reacted with chlorine gas in the presence of at least one member selected from the group consisting of oxygen and water.

6. The process for preparing a half-vanadocene compound according to item 5, wherein the half-vanadocene compound to be obtained is a compound represented by the formula (3)

$$CpVOCl_2 \quad (3)$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl.

7. The process for preparing a half-vanadocene compound according any of items 1 to 4, wherein the vanadocene compound represented by the formula (1) is reacted with chlorine gas in the absence of oxygen and water.

8. The process for preparing a half-vanadocene compound according to item 7, wherein the half-vanadocene compound to be obtained is a compound represented by the formula (2)

$$CPVCl_3 \quad (2)$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl.

9. A process for preparing a half-vanadocene compound according to any of items of 1 to 8, wherein the process further comprises the step of reacting a vanadium compound represented by the formula (4)

$$VX_4 \quad (4)$$

wherein X represents fluorine, chlorine, bromine or iodine, and the four X atoms may be the same or different with at least one of alkali metal compounds represented by the formula (5)

$$CpM \quad (5)$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl, M represents lithium, sodium, potassium, rubidium or cesium to obtain a vanadocene compound represented by the formula (1)

$$Cp_2VX_2 \quad (1)$$

wherein Cp and X are as defined in claim 1.

According to the invention of item 1, a half-vanadocene compound can be easily prepared with a high purity in a high yield by using a vanadocene compound of the formula (1) ($Cp_2VX_2$) which is chemically stable, and by reacting the vanadocene compound of the formula (1) with chlorine gas.

The process of the invention is simplified and the reaction conditions can be easily controlled and therefore the process gives a half-vanadocene compound on a mass-production basis.

As described above, a high purity half-vanadocene compound can be produced on a mass-production basis according to the producing process of the invention, and the obtained half-vanadocene compound can be provided in various fields such as a catalyst to be used in organic synthesis (especially a catalyst for polymerization of olefins or diolefins).

According to the invention of item 5, a half-vanadocene compound represented by the formula $CpVOCl_2$ can be easily prepared with a high purity in a high yield by reacting the vanadocene compound represented by the formula (1) with chlorine gas in the presence of oxygen and/or water.

According to the invention of item 7, a half-vanadocene compound represented by the formula $CpVCl_3$ can be easily prepared with a high purity in a high yield by reacting the vanadocene compound represented by the formula (1) with chlorine in the absence of oxygen and water.

In the process of the invention, it is preferable that a vanadium compound ($VX_4$) is reacted with an alkali metal compound (CpM) to give a vanadocene compound ($Cp_2VX_2$) as set forth in item 9. In this reaction, an alkali metal salt (MX) is produced as a by-product, but does not interfere with the chlorination of vanadocene compound ($Cp_2VX_2$) with chlorine gas in the next step. Thus, the obtained vanadocene compound represented by the formula (1) ($Cp_2VX_2$) can be reacted, without its purification, with chlorine gas, whereby the producing process can be simplified.

In the process of this invention, the vanadium compound ($VX_4$) generally used as an industrial raw material can be used as the raw material, and therefore the vanadocene compound ($Cp_2VX_2$) and the half-vanadocene compound prepared therefrom can be mass-produced. Furthermore the reaction conditions can be easily controlled in the reaction between the vanadocene compound ($Cp_2VX_2$) and chlorine gas. Therefore a half-vanadocene compound can be easily prepared with a high purity in a high yield.

DETAILED DESCRIPTION OF THE INVENTION

The process for preparing a half-vanadocene compound according to the invention includes a step of chlorinating a vanadocene compound represented by the formula (1)

$$Cp_2VX_2 \quad (1)$$

wherein Cp and X are as defined above.

In the process of the invention, especially, chlorine gas is used for chlorination.

Vanadocene Compound

X in the formula (1) represents fluorine, chlorine, bromine or iodine, and the two X atoms may be the same or different. X is preferably chlorine or bromine, more preferably chlorine.

Cp in the formula (1) represents a group having a cyclopentadienyl skeleton. More specifically, Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl, and the two Cp groups may be the same or different. Cp is preferably cyclopentadienyl or substituted cyclopentadienyl, and more preferably cyclopentadienyl.

When Cp in the formula (1) is a group having one or more substituents, preferred substituents are selected from the group consisting of hydrocarbon groups having 1 to 20 carbon atoms and silicon-containing hydrocarbon groups having 1 to 20 carbon atoms.

Preferred examples of hydrocarbon groups having 1 to 20 carbon atoms include:
- alkyl groups having 1 to 20 carbon atoms, especially alkyl groups having 1 to 8 carbon atoms, such as methyl, ethyl, n-propyl, iso-propyl, n-butyl, iso-butyl, sec-butyl, t-butyl, n-pentyl, iso-pentyl, neo-pentyl, tert-pentyl, n-hexyl, iso-hexyl, octyl and like;
- aralkyl groups, especially phenyl-$C_1$–$C_4$ alkyl groups, such as benzyl;
- aryl groups having 6 to 20, especially 6 to 12, carbon atoms including phenyl optionally substituted with 1 to 3 $C_1$–$C_4$ alkyl groups, such as toluyl, phenyl, 2,6-dimethylphenyl, 2,6-di-iso-propyl-phenyl, mesityl, as well as naphthyl and the like; adamantyl and the like.

Among the silicon-containing hydrocarbon groups having 1 to 20 carbon atoms, preferred are hydrocarbon groups having 3 to 12 carbon atoms, and 1 or 2 silicon atoms such as trimethylsilyl, trimethylsilylmethyl, bis(trimethylsilyl)methyl and the like.

Among the foregoing substituents, methyl, ethyl, n-propyl, iso-propyl, n-butyl, iso-butyl, sec-butyl, t-butyl and phenyl are preferred. Methyl, iso-propyl and t-butyl are more preferred.

The substituted cyclopentadienyl group may have 1 to 5 substituents, preferably 1 or 2 substituents. The substituted indenyl group may have 1 to 6 substituents, preferably 1 to 3 substituents. The substituted fluorenyl group may have 1 to 8 substituents, preferably 1 or 2 substituents. The substituted benzoindenyl group may have 1 to 8 substituents, preferably 1 or 2 substituents. The substituted azulenyl group may have 1 to 7 substituents, preferably 1 or 2 substituents.

Specific examples of the substituted cyclopentadienyl group are methylcyclopentadienyl, 1,2-dimethylcyclopentadienyl, 1,3-dimethylcyclopentadienyl, 1,2,3-trimethylcyclopentadienyl, 1,2,4-trimethylcyclopentadienyl, tetramethylcyclopentadienyl, pentamethylcyclopentadienyl, 1-methyl-2-ethylcyclopentadienyl, 1-methyl-3-ethylcyclopentadienyl, 1-methyl-2-propylcyclopentadienyl, 1-methyl-3-propylcyclopentadienyl, ethylcyclopentadienyl, 1,2-diethylcyclopentadienyl, 1,3-diethylcyclopentadienyl, 1,2-di-n-propylcyclopentadienyl, 1,3-di-n-propylcyclopentadienyl, 1,2-di-iso-propylcyclopentadienyl, 1,3-di-iso-propylcyclopentadienyl, 1,2-di-n-butylcyclopentadienyl, 1,3-di-n-butylcyclopentadienyl, 1,3-di-t-butylcyclopentadienyl, n-pentylcyclopentadienyl, n-hexylcyclopentadienyl, n-octylcyclopentadienyl, phenylcyclopentadienyl, benzylcyclopentadienyl, trimethylsilylcyclopentadienyl, 1,3-bis(trimethylsilyl)cyclopentadienyl, trimethylsilylmethylcyclopentadienyl, bis(trimethylsilyl)methylcyclopentadienyl, etc.

Among them, methylcyclopentadienyl, 1,2-dimethylcyclopentadienyl, 1,3-dimethylcyclopentadienyl, 1,2,3-trimethylcyclopentadienyl, 1,2,4-trimethylcyclopentadienyl, tetramethylcyclopentadienyl., pentamethylcyclopentadienyl and ethylcyclopentadienyl are preferred. methylcyclopentadienyl is more preferred.

Specific examples of the substituted indenyl group are 2-methylindenyl, 2-ethylindenyl, 2-n-propylindenyl, 2-iso-propylindenyl, 2-n-butylindenyl, 2-t-butylindenyl, 2-trimethylsilylindenyl, 2,4-dimethylindenyl, 2-methyl-4-phenylindenyl, tetrahydroindenyl, etc. Among them, 2-methylindenyl, 2-iso-propylindenyl, 2-t-butylindenyl and tetrahydroindenyl are preferred. 2-methylindenyl and tetrahydroindenyl are more preferred.

Specific examples of the substituted fluorenyl group are 9-methylfluorenyl, 9-ethylfluorenyl, 9-n-propylfluorenyl, 9-iso-propylfluorenyl, 9-n-butylfluorenyl, 9-methyl-1-methylfluorenyl, octahydrofluorenyl, etc. Among them, 9-methylfluorenyl, 9-iso-propylfluorenyl and octahydrofluorenyl are preferred. 9-methylfluorenyl and octahydrofluorenyl are more preferred.

Preferred examples of the substituted benzoindenyl group are 2-methylbenzoindenyl, 2-ethylbenzoindenyl, 2-n-propylbenzoindenyl, 2-iso-propylbenzoindenyl, 2-n-butylbenzoindenyl, 2-t-butylbenzoindenyl, etc. Among them, 2-methylbenzoindenyl, 2-iso-propylbenzoindenyl and 2-t-butylbenzoindenyl are preferred. 2-methylbenzoindenyl is more preferred.

Preferred examples of the substituted azulenyl group are 2-methylazulenyl, 2-ethylazulenyl, 2-n-propylazulenyl, 2-iso-propylazulenyl, 4,8-dimethylazulenyl, 2,4,8-trimethylazulenyl, 4,8-dimethyl-2-iso-propylazulenyl, etc. Among them, 2-methylazulenyl and 2-iso-propylazulenyl are preferred and 2-methylazulenyl is more preferred.

In view of the above, examples of preferable vanadocene compounds include $(C_5H_5)_2VF_2$, $(C_5H_5)_2VCl_2$, $(C_5H_5)_2VBr_2$, $(C_5H_5)_2VI_2$, $(CH_3C_5H_4)_2VF_2$, $(CH_3C_5H_4)_2VCl_2$, $(CH_3C_5H_4)_2VBr_2$, $(CH_3C_5H_4)_2VI_2$, $[1,2\text{-}(CH_3)_2C_5H_3]_2VF_2$, $[1,2\text{-}(CH_3)_2C_5H_3]_2VCl_2$, $[1,2\text{-}(CH_3)_2C_5H_3]_2VBr_2$, $[1,2\text{-}(CH_3)_2C_5H_3]_2VI_2$, $[1,3\text{-}(CH_3)_2C_5H_3]_2VF_2$, $[1,3\text{-}(CH_3)_2C_5H_3]_2VCl_2$, $[1,3\text{-}(CH_3)_2C_5H_3]_2VBr_2$, $[1,3\text{-}(CH_3)_2C_5H_3]_2VI_2$, $[1,2,3\text{-}(CH_3)_3C_5H_2]_2VF_2$, $[1,3\text{-}(CH_3)_3C_5H_2]_2VCl_2$, $[1,2,3\text{-}(CH_3)_3C_5H_2]_2VBr_2$, $[1,2,3\text{-}(CH_3)_3C_5H_2]_2VI_2$, $[1,2,4\text{-}(CH_3)_3C_5H_2]_2VF_2$, $[1,2,4\text{-}(CH_3)_3C_5H_2]_2VCl_2$, $[1,2,4\text{-}(CH_3)_3C_5H_2]_2VBr_2$, $[1,2,4\text{-}(CH_3)_3C_5H_2]_2VI_2$, $[(CH_3)_4C_5H]_2VF_2$, $[(CH_3)_4C_5H]_2VCl_2$, $[(CH_3)_4C_5H]_2VBr_2$, $[(CH_3)_4C_5H]_2VI_2$, $[(CH_3)_5C_5]_2VF_2$, $[(CH_3)_5C_5]_2VCl_2$, $[(CH_3)_5C_5]_2VBr_2$, $(1\text{-}CH_3\text{-}2\text{-}C_2H_5C_5H_3)_2VI_2$, $(1\text{-}CH_3\text{-}2\text{-}C_2H_5C_5H_3)_2VF_2$, $(1\text{-}CH_3\text{-}2\text{-}C_2H_5C_5H_3)_2VCl_2$, $(1\text{-}CH_3\text{-}2\text{-}C_2H_5C_5H_3)_2VBr_2$, $(1\text{-}CH_3\text{-}2\text{-}C_2H_5C_5H_3)_2VI_2$, $(1\text{-}CH_3\text{-}3\text{-}C_2H_5C_5H_3)_2VF_2$, $(1\text{-}CH_3\text{-}3\text{-}C_2H_5C_5H_3)_2VCl_2$, $(1\text{-}CH_3\text{-}3\text{-}C_2H_5C_5H_3)_2VBr_2$, $(1\text{-}CH_3\text{-}3\text{-}C_2H_5C_5H_3)_2VI_2$, $(1\text{-}CH_3\text{-}2\text{-}n\text{-}C_3H_7C_5H_3)_2VF_2$, $(1\text{-}CH_3\text{-}2\text{-}n\text{-}C_3H_7C_5H_3)_2VCl_2$, $(1\text{-}CH_3\text{-}2\text{-}n\text{-}C_3H_7C_5H_3)_2VBr_2$, $(1\text{-}CH_3\text{-}2\text{-}n\text{-}C_3H_7C_5H_3)_2VBr_2$, $(1\text{-}CH_3\text{-}2\text{-}n\text{-}C_3H_7C_5H_3)_2VI_2$, $(1\text{-}CH_3\text{-}2\text{-}iso\text{-}C_3H_7C_5H_3)_2VF_2$, $(1\text{-}CH_3\text{-}2\text{-}iso\text{-}C_3H_7C_5H_3)_2VCl_2$, $(1\text{-}CH_3\text{-}2\text{-}iso\text{-}C_3H_7C_5H_3)_2VBr_2$, $(1\text{-}CH_3\text{-}2\text{-}iso\text{-}C_3H_7C_5H_3)_2VI_2$, $(1\text{-}CH_3\text{-}3\text{-}n\text{-}C_3H_7C_5H_3)_2VF_2$, $(1\text{-}CH_3\text{-}3\text{-}n\text{-}C_3H_7C_5H_3)_2VCl_2$, $(1\text{-}CH_3\text{-}3\text{-}n\text{-}C_3H_7C_5H_3)_2VBr_2$, $(1\text{-}CH_3\text{-}3\text{-}n\text{-}C_3H_7C_5H_3)_2VI_2$, $(1\text{-}CH_3\text{-}3\text{-}iso\text{-}C_3H_7C_5H_3)_2VF_2$, $(1\text{-}CH_3\text{-}iso\text{-}C_3H_7C_5H_3)_2VCl_2$, $(1\text{-}CH_3\text{-}3\text{-}iso\text{-}C_3H_7C_5H_3)_2VBr_2$, (1-CH$_3$-3-iso-C$_3$H$_7$C$_5$H$_3$)$_2$VI$_2$, (C$_2$H$_5$C$_5$H$_4$)$_2$VF$_2$ (C$_2$H$_5$C$_5$H$_4$)$_2$VCl$_2$(C$_2$H$_5$C$_5$H$_4$)$_2$VBr$_2$(C$_2$H$_5$C$_5$H$_4$)$_2$VI$_2$, [1,2-(C$_2$H$_5$)$_2$C$_5$H$_3$]$_2$VF$_2$, [1,2-(C$_2$H$_5$)$_2$C$_5$H$_3$]$_2$VCl$_2$, [1,2-(C$_2$H$_5$)$_2$C$_5$H$_3$]$_2$VBr$_2$, [1,2-(C$_2$H$_5$)$_2$C$_5$H$_3$]$_2$VI$_2$, [1,3-(C$_2$H$_5$)$_2$C$_5$H$_3$]$_2$VF$_2$, [1,3-(C$_2$H$_5$)$_2$C$_5$H$_3$]$_2$VCl$_2$, [1,3-(C$_2$H$_5$)$_2$C$_5$H$_3$]$_2$VBr$_2$, [1,3-(C$_2$H$_5$)$_2$C$_5$H$_3$]$_2$VI$_2$, [1,2-(n-C$_3$H$_7$)$_2$C$_5$H$_3$]$_2$VF$_2$, [1,2-(n-C$_3$H$_7$)$_2$C$_5$H$_3$]$_2$VCl$_2$, [1,2-(n-C$_3$H$_7$)$_2$C$_5$H$_3$]$_2$VBr$_2$, [1,2-(n-C$_3$H$_7$)$_2$C$_5$H$_3$]$_2$VI$_2$, [1,3-(n-C$_3$H$_7$)$_2$C$_5$H$_3$]$_2$VF$_2$, [1,3-(n-C$_3$H$_7$)$_2$C$_5$H$_3$]$_2$VCl$_2$, [1,3-(n-C$_3$H$_7$)$_2$C$_5$H$_3$]$_2$VBr$_2$, [1,3-(n-C$_3$H$_7$)$_2$C$_5$H$_3$]$_2$VI$_2$, [1,2-(iso-C$_3$H$_7$)$_2$C$_5$H$_3$]$_2$VF$_2$, [1,2-(iso-C$_3$H$_7$)$_2$C$_5$H$_3$]$_2$VCl$_2$, [1,2-(iso-C$_3$H$_7$)$_2$C$_5$H$_3$]$_2$VBr$_2$, [1,2-(iso-C$_3$H$_7$)$_2$C$_5$H$_3$]$_2$VI$_2$, [1,3-(iso-C$_3$H$_7$)$_2$C$_5$H$_3$]$_2$VF$_2$, [1,3-(iso-C$_3$H$_7$)$_2$C$_5$H$_3$]$_2$VCl$_2$, [1,3-(iso-C$_3$H$_7$)$_2$C$_5$H$_3$]$_2$VBr$_2$, [1,3-(iso-C$_3$H$_7$)$_2$C$_5$H$_3$]$_2$VI$_2$, [1,2-(n-C$_4$H$_9$)$_2$C$_5$H$_3$]$_2$VF$_2$, [1,2-(n-C$_4$H$_9$)$_2$C$_5$H$_3$]$_2$VCl$_2$, [1,2-(n-C$_4$H$_9$)$_2$C$_5$H$_3$]$_2$VBr$_2$, [1,2-(n-C$_4$H$_9$)$_2$C$_5$H$_3$]$_2$VI$_2$, [1,3-(n-C$_4$H$_9$)$_2$C$_5$H$_3$]$_2$VF$_2$, [1,3-(n-C$_4$H$_9$)$_2$C$_5$H$_3$]$_2$VCl$_2$, [1,3-(n-C$_4$H$_9$)$_2$C$_5$H$_3$]$_2$VBr$_2$, [1,3(n-C$_4$H$_9$)$_2$C$_5$H$_3$]$_2$VI$_2$, [1,3-(t-C$_4$H$_9$)$_2$C$_5$H$_3$]$_2$VF$_2$, [1,3-(t-C$_4$H$_9$)$_2$ C$_5$H$_3$]$_2$VCl$_2$, [1,3(t-C$_4$H$_9$)$_2$C$_5$H$_3$]$_2$VBr$_2$, [1,3-(t-C$_4$H$_9$)$_2$C$_5$H$_3$]$_2$VI$_2$, (n-C$_5$H$_{11}$C$_5$H$_4$)$_2$VF$_2$, (n-C$_5$H$_{11}$C$_5$H$_4$)$_2$VCl$_2$, (n-C$_5$H$_{11}$C$_5$H$_4$)$_2$VBr$_2$, (n-C$_5$H$_4$)$_2$VI$_2$, (n-C$_6$H$_{13}$C$_5$H$_4$)$_2$ VF$_2$, (n-C$_6$H$_{13}$C$_5$H$_4$)$_2$VCl$_2$, (n-C$_6$H$_{13}$C$_5$H$_4$)$_2$VBr$_2$, (n-C$_6$H$_{13}$C$_5$H$_4$)$_2$VI$_2$, (n-C$_8$H$_{17}$C$_5$H$_4$)$_2$ VF$_2$, (n-C$_8$H$_{17}$C$_5$H$_4$)$_2$VCl$_2$, (n-C$_8$H$_{17}$C$_5$H$_4$)$_2$VBr$_2$, (n-C$_8$H$_{17}$C$_5$H$_4$)$_2$VI$_2$, (C$_6$H$_5$C$_5$H$_4$)$_2$ VF$_2$, (C$_6$H$_5$C$_5$H$_4$)$_2$VCl$_2$, (C$_6$H$_5$C$_5$H$_4$)$_2$VBr$_2$, (C$_6$H$_5$C$_5$H$_4$)$_2$ VI$_2$, (C$_6$H$_5$CH$_2$C$_5$H$_4$)$_2$VF$_2$, (C$_6$H$_5$C$_5$H$_4$)$_2$VCl$_2$, (C$_6$H$_5$CH$_2$C$_5$H$_4$)$_2$VBr$_2$, (C$_6$H$_5$CH$_2$C$_5$H$_4$)$_2$VI$_2$, [(CH$_3$)$_3$ SiC$_5$H$_4$]$_2$VF$_2$, [(CH$_3$)$_3$SiC$_5$H$_4$]$_2$VCl$_2$, [(CH$_3$)$_3$SiC$_5$H$_4$]$_2$ VBr$_2$, [(CH$_3$)$_3$SiC$_5$H$_4$]$_2$VI$_2$, {1,3-[(CH$_3$)$_3$Si]$_2$C$_5$H$_3$}$_2$VF$_2$, {1,3-[(CH$_3$)$_3$Si]$_2$C$_5$H$_3$}$_2$VCl$_2$, {1,3-[(CH$_3$)$_3$Si]$_2$ C$_5$H$_3$}$_2$VBr$_2$, {1,3-[(CH$_3$)$_3$Si]$_2$C$_5$H$_3$}$_2$VI$_2$, [(CH$_3$)$_3$Si(CH$_3$) C$_5$H$_3$]$_2$VF$_2$[1-(CH$_3$)$_3$Si-3-CH$_3$C$_5$H$_3$]$_2$VCl$_2$, [1-(CH$_3$)$_3$Si-3-CH$_3$C$_5$H$_3$]$_2$VBr$_2$, [1-(CH$_3$)$_3$Si-3-CH$_3$C$_5$H$_3$]$_2$VI$_2$, {1,3-[(CH$_3$)$_3$Si]$_2$-4-CH$_3$C$_5$H$_2$}$_2$VF$_2$ {1,3-[(CH$_3$)$_3$Si]$_2$-4-CH$_3$C$_5$H$_2$}$_2$VCl$_2$, {1,3-[(CH$_3$)$_3$Si]$_2$-4-CH$_3$C$_5$H$_2$}$_2$VBr$_2$, {1,3-[(CH$_3$)$_3$Si]$_2$-4-CH$_3$C$_5$H$_2$}$_2$VI$_2$, Ind$_2$VF$_2$, Ind$_2$VCl$_2$, Ind$_2$VBr$_2$, Ind$_2$VI$_2$, (2-CH$_3$Ind)$_2$VF$_2$, (2-CH$_3$Ind)$_2$VCl$_2$, (2-CH$_3$Ind)$_2$VBr$_2$, (2-CH$_3$Ind)$_2$VI$_2$, (2-C$_2$H$_5$Ind)$_2$VF$_2$, (2-C$_2$H$_5$Ind)$_2$VCl$_2$, (2-C$_2$H$_5$Ind)$_2$VBr$_2$, (2-C$_2$H$_5$Ind)$_2$VI$_2$, (2-n-C$_3$H$_7$Ind)$_2$VF$_2$, (2-n-C$_3$H$_7$Ind)$_2$VCl$_2$, (2-n-C$_3$H$_7$Ind)$_2$ VCl$_2$, (2-n-C$_3$H$_7$Ind)$_2$VBr$_2$, (2-n-C$_3$H$_7$Ind)$_2$VI$_2$, (2-iso-C$_3$H$_7$Ind)$_2$VF$_2$, (2-iso-C$_3$H$_7$Ind)$_2$VCl$_2$, (2-iso-C$_3$H$_7$Ind)$_2$ VBr$_2$, (2-iso-C$_3$H$_7$Ind)$_2$VI$_2$, (2-n-C$_4$H$_9$Ind)$_2$VF$_2$, (2-n-C$_4$H$_9$Ind)$_2$VCl$_2$, (2-n-C$_4$H$_9$Ind)$_2$VBr$_2$, (2-n-C$_4$H$_9$Ind)$_2$VI$_2$, (2-t-C$_4$H$_9$Ind)$_2$VF$_2$, (2-t-C$_4$H$_9$Ind)$_2$VCl$_2$, (2-t-C$_4$H$_9$Ind)$_2$ VBr$_2$, (2-t-C$_4$H$_9$Ind)$_2$VI$_2$, [2-(CH$_3$)$_3$SiInd)]$_2$VF$_2$, [2-(CH$_3$)$_3$ SiInd)]$_2$VCl$_2$, [2-(CH$_3$)$_3$SiInd)]$_2$VBr$_2$[2-(CH$_3$)$_3$SiInd)]$_2$VI$_2$, [2,4-(CH$_3$)$_2$Ind)]$_2$VF$_2$, [2,4-(CH$_3$)$_2$Ind)]$_2$VCl$_2$, [2,4-(CH$_3$)$_2$ Ind)]$_2$VBr$_2$, [2,4-(CH$_3$)$_2$Ind)]$_2$VI$_2$, (2-CH$_3$-4-C$_6$H$_5$Ind)$_2$ VF$_2$, (2-CH$_3$-4-C$_6$H$_5$Ind)$_2$VCl$_2$, (2-CH$_3$-4-C$_6$H$_5$Ind)$_2$VBr$_2$, (2-CH$_3$-4-C$_6$H$_5$Ind)$_2$VI$_2$, (H$_4$Ind)$_2$VF$_2$, (H$_4$Ind)$_2$VCl$_2$, (H$_4$Ind)$_2$VBr$_2$, (H$_4$Ind)$_2$VI$_2$, Flu$_2$VF$_2$, Flu$_2$VCl$_2$, Flu$_2$VBr$_2$, Flu$_2$VI$_2$, (9-CH$_3$Flu)$_2$VF$_2$, (9-CH$_3$Flu)$_2$VCl$_2$, (9-CH$_3$Flu)$_2$ VBr$_2$, (9-CH$_3$Flu)$_2$VI$_2$, (9-C$_2$H$_5$Flu)$_2$VF$_2$, (9-C$_2$H$_5$Flu)$_2$ VCl$_2$, (9-C$_2$H$_5$Flu)$_2$VBr$_2$, (9-C$_2$H$_5$Flu)$_2$VI$_2$, (9-n-C$_3$H$_7$Flu)$_2$ VF$_2$, (9-n-C$_3$H$_7$Flu)$_2$VCl$_2$, (9-n-C$_3$H$_7$Flu)$_2$VBr$_2$,(9-n-C$_3$H$_7$Flu)$_2$VI$_2$, (9-iso-C$_3$H$_7$Flu)$_2$VF$_2$, (9-iso-C$_3$H$_7$Flu)$_2$ VCl$_2$, (9-iso-C$_3$H$_7$Flu)$_2$VBr$_2$, (9-iso-C$_3$H$_7$Flu)$_2$VI$_2$, (9-n-C$_4$H$_9$Flu)$_2$VF$_2$, (9-n-C$_4$H$_9$Flu)$_2$VCl$_2$, (9-n-C$_4$H$_9$Flu)$_2$VBr$_2$, (9-n-C$_4$H$_9$Flu)$_2$VI$_2$, [1,9-(CH$_3$)$_2$Flu]$_2$VF$_2$, [1,9-(CH$_3$)$_2$Flu]$_2$ VCl$_2$, [1,9-(CH$_3$)$_2$Flu]$_2$VBr$_2$, [1,9-(CH$_3$)$_2$Flu]$_2$VI$_2$, (H$_8$Flu)$_2$ VF$_2$, (H$_8$Flu)$_2$VCl$_2$, (H$_8$Flu)$_2$VBr$_2$, (H$_8$Flu)$_2$VI$_2$, Bind$_2$VF$_2$, Bind$_2$VCl$_2$, Bind$_2$VBr$_2$, Bind$_2$VI$_2$, (2-CH$_3$Bind)$_2$ VF$_2$, (2-CH$_3$Bind)$_2$VCl$_2$, (2-CH$_3$Bind)$_2$VBr$_2$, (2-CH$_3$Bind)$_2$VI$_2$, (2-C$_2$H$_5$Bind)$_2$VF$_2$, (2-C$_2$H$_5$Bind)$_2$VCl$_2$, (2-C$_2$H$_5$Bind)$_2$VBr$_2$, (2-C$_2$H$_5$Bind)$_2$VI$_2$, (2-n-C$_3$ H$_7$Bind)$_2$ VF$_2$, (2-n-C$_3$H$_7$Bind)$_2$VCl$_2$, (2-n-C$_3$H$_7$Bind)$_2$ VBr$_2$, (2-n-C$_3$H$_7$Bind)$_2$VI$_2$, (2-iso-C$_3$H$_7$Bind)$_2$VF$_2$, (2-iso-C$_3$H$_7$Bind)$_2$ VCl$_2$, (2-iso-C$_3$H$_7$Bind)$_2$VBr$_2$, (2-iso-C$_3$H$_7$Bind)$_2$VI$_2$, (2-n-C$_4$H$_9$Bind)$_2$VF$_2$, (2-n-C$_4$H$_9$Bind)$_2$ VCl$_2$, (2-n-C$_4$H$_9$Bind)$_2$VBr$_2$, (2-n-C$_4$H$_9$Bind)$_2$VI$_2$, (2-t-C$_4$H$_9$Bind)$_2$VF$_2$, (2-t-C$_4$H$_9$Bind)$_2$VCl$_2$, (2-t-C$_4$H$_9$Bind)$_2$ VBr$_2$, (2-t-C$_4$H$_9$Bind)$_2$VI$_2$, Azu$_2$VF$_2$, Azu$_2$VCl$_2$, Azu$_2$VBr$_2$, Azu$_2$VI$_2$, (2-CH$_3$Azu)$_2$VF$_2$, (2-CH$_3$Azu)$_2$VCl$_2$, (2-CH$_3$Azu)$_2$VBr$_2$, (2-CH$_3$Azu)$_2$VI$_2$, (2-C$_2$H$_5$Azu)$_2$VF$_2$, (2-C$_2$H$_5$Azu)$_2$VCl$_2$, (2-C$_2$H$_5$Azu)$_2$VBr$_2$, (2-C$_2$H$_5$Azu)$_2$VI$_2$, (2-n-C$_3$H$_7$Azu)$_2$VF$_2$, (2-n-C$_3$H$_7$Azu)$_2$VCl$_2$, (2-n-C$_3$H$_7$Azu)$_2$ VBr$_2$, (2-n-C$_3$H$_7$Azu)$_2$VI$_2$, (2-iso-C$_3$H$_7$Azu)$_2$ VF$_2$, (2-iso-C$_3$H$_7$Azu)$_2$VCl$_2$, (2-iso-C$_3$H$_7$Azu)$_2$VBr$_2$, (2-iso-C$_3$H$_7$Azu)$_2$VI$_2$, (4,8-(CH$_3$)$_2$Azu)$_2$VF$_2$, (4,8-(CH$_3$)$_2$ Azu)$_2$VCl$_2$, (4,8-(CH$_3$)$_2$Azu)$_2$VBr$_2$, (4,8-(CH$_3$)$_2$Azu)$_2$VI$_2$, (2,4,8-(CH$_3$)$_3$Azu)$_2$VF$_2$, (2,4,8-(CH$_3$)$_3$Azu)$_2$VCl$_2$, (2,4,8-(CH$_3$)$_3$Azu)$_2$VBr$_2$, (2,4,8-(CH$_3$)$_3$Azu)$_2$VI$_2$, [2-iso-C$_3$H$_7$-4,8-(CH$_3$)$_2$Azu]$_2$VF$_2$, [2-iso-C$_3$H$_7$-4,8-(CH$_3$)$_2$Azu]$_2$VCl$_2$, [2-iso-C$_3$H$_7$-4,8-(CH$_3$)$_2$Azu]$_2$VBr$_2$, and [2-iso-C$_3$H$_7$-4,8-(CH$_3$)$_2$Azu]$_2$VI$_2$.

In the above formulas, Ind represents indenyl, Flu represents fluorenyl, Bind represents benzoindenyl, Azu represents azulenyl, H$_4$Ind represents the following group (6)

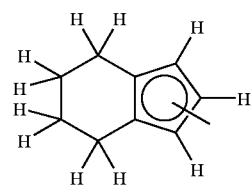

and H$_8$Flu represents the following group. (7).

(7)

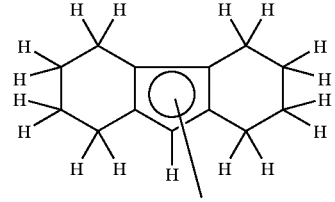

More preferred are (C$_5$H$_5$)$_2$VCl$_2$, (C$_5$H$_5$)$_2$VBr$_2$, (CH$_3$C$_5$H$_4$)$_2$VCl$_2$, (CH$_3$C$_5$H$_4$)$_2$VBr$_2$, [1,2-(CH$_3$)$_2$C$_5$H$_3$]$_2$ VCl$_2$, [1,2-(CH$_3$)$_2$C$_5$H$_3$]$_2$VBr$_2$, [1,3-(CH$_3$)$_2$C$_5$H$_3$]$_2$VCl$_2$, [1,3-(CH$_3$)$_2$C$_5$H$_3$]$_2$VBr$_2$, [1,2,3-(CH$_3$)$_3$C$_5$H$_2$]$_2$VCl$_2$, [1,2,3-(CH$_3$)$_3$C$_5$H$_2$]$_2$VBr$_2$, [1,2,4-(CH$_3$)$_3$C$_5$H$_2$]$_2$VCl$_2$, [1,2,4-(CH$_3$)$_3$C$_5$H$_2$]$_2$VBr$_2$, [(CH$_3$)$_4$C$_5$H]$_2$VCl$_2$, [(CH$_3$)$_4$C$_5$]$_2$VBr$_2$, [(CH$_3$)$_5$C$_5$]$_2$VCl$_2$, [(CH$_3$)$_5$C$_5$]$_2$VBr$_2$, (1-CH$_3$-2-C$_2$H$_5$C$_5$H$_3$)$_2$ VCl$_2$, (1-CH$_3$-2-C$_2$H$_5$C$_5$H$_3$)$_2$VBr$_2$, (1-CH$_3$-3-C$_2$H$_5$C$_5$H$_3$)$_2$VCl$_2$, (1-CH$_3$-3-C$_2$H$_5$C$_5$H$_3$)$_2$VBr$_2$, (1-CH$_3$-2-C$_3$H$_7$C$_5$H$_3$)$_2$VCl$_2$, (1-CH$_3$-2-C$_3$H$_7$C$_5$H$_3$)$_2$VBr$_2$, (1-CH$_3$-2-n-C$_3$H$_7$C$_5$H$_3$)$_2$VCl$_2$, (1-CH$_3$-2-n-C$_3$H$_7$C$_5$H$_3$)$_2$VBr$_2$, (1-CH$_3$-3-iso-C$_3$H$_7$C$_5$H$_3$)$_2$VCl$_2$, (1-CH$_3$-3-iso-C$_3$H$_7$C$_5$H$_3$)$_2$ VBr$_2$, (C$_2$H$_5$C$_5$H$_4$)$_2$VCl$_2$, (C$_2$H$_5$C$_5$H$_4$)$_2$VBr$_2$, [1,2-(C$_2$H$_5$)$_2$ C$_5$H$_3$]$_2$VCl$_2$, [1,2-(C$_2$H$_5$)$_2$C$_5$H$_3$]$_2$VBr$_2$, [1,3-(C$_2$H$_5$)$_2$ C$_5$H$_3$]$_2$ VCl$_2$, [1,3-(C$_2$H$_5$)$_2$C$_5$H$_3$]$_2$VBr$_2$, [1,2-(n-C$_3$H$_7$)$_2$ C$_5$H$_3$]$_2$VCl$_2$, [1,2-(n-C$_3$H$_7$)$_2$C$_5$H$_3$]$_2$VBr$_2$, [1,3-(n-C$_3$H$_7$)$_2$ C$_5$H$_3$]$_2$VCl$_2$, [1,3-(n-C$_3$H$_7$)$_2$C$_5$H$_3$]$_2$VBr$_2$, [1,2-(iso-C$_3$H$_7$)$_2$ C$_5$H$_3$]$_2$VCl$_2$, [1,2-(iso-C$_3$H$_7$)$_2$C$_5$H$_3$]$_2$VBr$_2$, [1,3-(iso-C$_3$H$_7$)$_2$ C$_5$H$_3$]$_2$VCl$_2$, [1,3-(iso-C$_3$H$_7$)$_2$C$_5$H$_3$]$_2$VBr$_2$, [1,2-(n-C$_4$H$_9$)$_2$ C$_5$H$_3$]$_2$VCl$_2$, [1,2-(n-C$_4$H$_9$)$_2$C$_5$H$_3$]$_2$VBr$_2$, [1,3-(n-C$_4$H$_9$)$_2$ C$_5$H$_3$]$_2$VCl$_2$, [1,3-(n-C$_4$H$_9$)$_2$C$_5$H$_3$]$_2$VBr$_2$, [1,3-(t-C$_4$H$_9$)$_2$ C$_5$H$_3$]$_2$VCl$_2$, [1,3-(t-C$_4$H$_9$)$_2$C$_5$H$_3$]$_2$VBr$_2$, (n-C$_5$H$_{11}$C$_5$H$_4$)$_2$ VCl$_2$, (n-C$_5$H$_{11}$C$_5$H$_4$)$_2$VBr$_2$, $(n-C_6H_{13}C_5H_4)_2VCl_2$, $(n-C_6H_{13}C_5H_4)_2VBr_2$, $(n-C_8H_{17}C_5H_4)_2VCl_2$, $(n-C_8H_{17}C_5H_4)_2VBr_2$, $(C_6H_5C_5H_4)_2VCl_2$, $(C_6H_5C_5H_4)_2VBr_2$, $(C_6H_5CH_2C_5H_4)_2VCl_2$, $(C_6H_5CH_2C_5H_4)_2VBr_2$, $[(CH_3)_3SiC_5H_4]_2VCl_2$, $[(CH_3)_3SiC_5H_4]_2VBr_2$, $\{1,3-[(CH_3)_3Si]_2C_5H_3\}_2VCl_2$, $\{1,3-[(CH_3)_3Si]_2C_5H_3\}_2VBr_2$, $[1-(CH_3)_3Si-3-CH_3C_5H_3]_2VCl_2$, $[1-(CH_3)_3Si-3-CH_3C_5H_3]_2VBr_2$, $\{1,3-[(CH_3)_3Si]_2-4-CH_3C_5H_2\}_2VCl_2$, and $\{1,3-[(CH_3)_3Si]_2-4-CH_3C_5H_2\}_2VBr_2$. Still more preferred is $(C_5H_5)_2VCl_2$.

Process for Preparing Vanadocene Compound ($CP_2VX_2$)

The vanadocene compound represented by the formula (1) ($Cp_2VX_2$) is preferably prepared according to a reaction scheme (I) shown below $$VX_4 + 2CpM \rightarrow Cp_2VX_2 + 2MX \qquad (I)$$

(4) (5) (1)

using a vanadium compound represented by the formula (4)

$$VX_4 \qquad (4)$$

wherein X is as defined above and an alkali metal compound represented by the formula (5)

$$CpM \qquad (5)$$

wherein Cp and M are as defined above.

Since the alkali metal salt (MX) is produced as a by-product in the reaction scheme (I), the obtained vanadocene compound ($Cp_2VX_2$) contains the alkali metal salt (MX) as impurity. However, the alkali metal salt (MX) does not hinder the chlorination reaction of the vanadocene compound ($Cp_2VX_2$) with chlorine gas, which is a feature of the invention. For this reason, the vanadocene compound ($Cp_2VX_2$) prepared by the reaction scheme (I) can be used in the invention without purification.

In view of the above, the purification of vanadocene compound ($Cp_2VX_2$) can be omitted in the process of the invention, whereby the process can be simplified and the costs can be lowered. In addition, the vanadium compound ($VX_4$) generally used as an industrial raw material can be used as the raw material, therefore the vanadocene compound ($Cp_2VX_2$) and the half-vanadocene compound prepared therefrom can be mass-produced.

In the present invention, preferably the vanadium compound represented by the formula (4) ($VX_4$) is reacted with an alkali metal compound represented by the formula (5) (CpM) to give a vanadocene compound ($Cp_2VX_2$). Described below is the process for preparing the vanadocene compound of the formula (1) ($Cp_2VX_2$) according to the reaction scheme (I).

In the formula (4), X represents fluorine, chlorine, bromine or iodine, and four X atoms may be the same or different. The X atoms may be those constituting the contemplated vanadocene compound of the formula (1). When two X atoms in the contemplated vanadocene compound of the formula (1) are different from each other, two kinds of vanadium compounds having different X atoms are used as mixed.

Examples of the vanadium compound ($VX_4$) are vanadium tetrafluoride, vanadium tetrachloride, vanadium tetrabromide, vanadium tetraiodide and the like. Among them, vanadium tetrachloride and vanadium tetrabromide are preferred, and vanadium tetrachloride is more preferred.

The vanadium compounds of the formula (4) ($VX_4$) are known and readily available.

In the formula (5), M represents lithium, sodium, potassium, rubidium or cesium. Among them, lithium, sodium and potassium are preferred, and lithium and sodium are more preferred. In the formula (5), Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl. As the Cp groups, the groups constituting the contemplated vanadocene compound ($Cp_2VX_2$) may be selected.

When two Cp groups in the contemplated vanadocene compound ($Cp_2VX_2$) are different from each other, two kinds of alkali metal compounds (CpM) having different Cp groups are used as mixed.

The alkali metal compounds represented by the formula (5) (CpM) are known and readily available.

The method of reaction between the vanadium compound ($VX_4$) and the alkali metal compound (CpM) is not limited. For example, the two compounds can be reacted by mixing a solution or a slurry of the vanadium compound ($VX_4$) and a solution or a slurry of the alkali metal compound (CpM), and stirring the resulting mixture.

In the reaction between the vanadium compound and alkali metal compound, there are no particular limitations on the reaction conditions e.g., the solvent to be used, concentration of each compound, molar ratio of vanadium compound/alkali metal compound, reaction temperature, reaction time, and the like. The reaction conditions can be suitably determined according to the desired product.

A variety of solvents can be used for dissolving or suspending the vanadium compound ($VX_4$) and the alkali metal compound (CpM). Among them, ethers and hydrocarbons are preferred. Specific examples of the solvent to be used are ethyl ether, butyl methyl ether, sec-butyl methyl ether, t-butyl methyl ether, t-amyl methyl ether, butyl ethyl ether, sec-butyl ethyl ether, t-butyl ethyl ether, propyl ether, iso-propyl ether, tetrahydrofuran, 2-methyl tetrahydrofuran, 2,5-dimethyl tetrahydrofuran, 1,3-dioxane, 1,4-dioxane, 4-methyl-1,3-dioxane, 1,3-dioxepane, toluene, xylene, hexane, heptane, octane, nonane, decane, etc. In the invention, ethyl ether and tetrahydrofuran are preferred.

The alkali metal compound (CpM) and the vanadium compound ($VX_4$) to be used as the raw materials are used, each in a concentration of preferably about 0.1 to about 3 moles/liter, more preferably about 0.2 to about 2 moles/liter. When the alkali metal compound (CpM) and the vanadium compound ($VX_4$) are used in the above-mentioned concentration range, the reaction easily proceeds and unreacted substances remain in a lesser amount or scarcely remain.

The alkali metal compound and the vanadium compound are used in a molar ratio ($CpM/VX_4$) of preferably about 0.5 to about 5, more preferably about 1.5 to about 3. Since the theoretical molar ratio of the alkali metal compound (CpM) to the vanadium compound ($VX_4$) is 2:1, the contemplated vanadocene compound ($Cp_2VX_2$) can be prepared with a high purity in a high yield by using the two compounds in the above-mentioned molar ratio.

The reaction temperature is in the range of preferably about −100 to about 100° C., more preferably about −50 to about 50° C. The reaction time is in the range of preferably about 1 to about 100 hours, more preferably about 2 to about 48 hours. When the reaction proceeds at said temperature, the reaction is unlikely to require excessively a prolonged time, and the purity of obtained vanadocene compound is unlikely to be lowered due to the production of by-products or decomposition of the vanadocene compound.

The foregoing reaction may be performed under atmospheric pressure, but preferably carried out under a pressure of about $5 \times 10^4$ to about $2 \times 10^5$ Pa.

The produced vanadocene compound ($Cp_2VX_2$) can be obtained by separation of insoluble solids precipitated from the reaction mixture through filtration or by evaporation of reaction mixture to dryness.

Chlorination of the Vanadocene Compound ($Cp_2VX_2$)

Description is given below on the method of reacting the vanadocene compound ($Cp_2VX_2$) with chlorine gas.

When the vanadocene compound ($Cp_2VX_2$) is reacted with chlorine gas with addition of oxygen and/or water to the reaction system, a half-vanadocene compound ($CpVOCl_2$) is produced. When the vanadocene compound is reacted with chlorine gas without addition of oxygen or water to the reaction system, a half-vanadocene compound ($CpVCl_3$) is produced.

The method of reacting the vanadocene compound ($Cp_2VX_2$) with chlorine gas is not limited. For example, the vanadocene compound ($Cp_2VX_2$) can be reacted with chlorine gas by supplying chlorine gas to a solution or a slurry of vanadocene compound ($Cp_2VX_2$).

When the vanadocene compound ($Cp_2VX_2$) is reacted with chlorine gas in the absence of oxygen and water, the reaction may be carried out under an atmosphere of inert gas such as rare gas or nitrogen gas.

When oxygen and/or water is mixed with the reaction system, chlorine gas can be supplied while continuously supplying oxygen and/or water to a solution or a slurry of the vanadocene compound ($CP_2VX_2$).

In the chlorination reaction of the vanadocene compound, there are no particular limitations on reaction conditions, such as the solvent to be used, concentration of vanadocene compound ($Cp_2VX_2$), molar ratio of vanadocene compound/chlorine ($Cp_2VX_2/Cl_2$), pressure of chlorine gas, reaction temperature, reaction time, molar ratio of vanadocene compound/oxygen ($Cp_2VX_2/O_2$) and molar ratio of vanadocene compound/water ($Cp_2VX_2/H_2O$) when the reaction is carried out in the presence of oxygen and/or water. These reaction conditions can be suitably determined according to the desired product.

Useful solvents include organic solvents which are inert to the chlorination reaction of the invention, preferably halogenated hydrocarbons or hydrocarbons. Examples of solvents are carbon tetrachloride, chloroform, methylene chloride, 1,2-dichloroethane, 1,1,1-trichloroethane, 1,1,2-trichloroethane, 1,1,1,2-tetrachloroethane, 1,1,2,2-tetrachloroethane, bromoform, dibromoethane, 1,2-dibromoethane, 1,1,2,2-tetrabromoethane and like halogenated hydrocarbons containing 1 to 4 halogen atoms and 1 to 4 carbon atoms; pentane, hexane, heptane, octane, nonane, decane and like hydrocarbons having 5 to 12 carbon atoms; etc. Among them, halogenated hydrocarbons are preferred, and chloroform and methylene chloride are more preferred.

The vanadocene compound ($Cp_2VX_2$) is used in a concentration of preferably about 0.02 to about 2 moles/liter, more preferably about 0.1 to about 1 mole/liter. When the concentration of the vanadocene compound ($Cp_2VX_2$) is in the foregoing range, the reaction easily proceeds, and unreacted substances remain in a lesser amount or scarcely remain.

The molar ratio of vanadocene compound/chlorine ($Cp_2VX_2/Cl_2$) is preferably 0.5 to about 20, more preferably about 1 to about 10. When the molar ratio of vanadocene compound/chlorine ($Cp_2VX_2/Cl_2$) is in the above-mentioned range, the contemplated compound can be efficiently produced in a high yield.

The method of supplying chlorine gas is not limited. For example, chlorine gas may be continuously supplied until the foregoing molar ratio is attained as a whole. Alternatively the required amount of chlorine gas may be supplied at one time. The pressure of chlorine gas in the reaction is preferably about 0.02 to about 2 MPa, more preferably about 0.05 to about 1 MPa.

The reaction temperature is in the range of preferably about −50 to about 150° C., more preferably about 0 to about 100° C. The reaction time is in the range of preferably about 30 minutes to about 48 hours, more preferably about 1 to about 24 hours.

When the vanadocene compound ($Cp_2VX_2$) is reacted with chlorine gas in the presence of oxygen, the molar ratio of vanadocene compound/oxygen ($Cp_2VX_2/O_2$) is preferably about 0.05 to about 2, more preferably about 0.1 to about 1. When the vanadocene compound ($CP_2VX_2$) is reacted with chlorine gas in the presence of water, the molar ratio of vanadocene compound/water ($Cp_2VX_2/H_2O$) is preferably about 0.1 to about 4, more preferably about 0.2 to about 2. When the vanadocene compound ($Cp_2VX_2$) is reacted with chlorine gas in the presence of oxygen and water, the molar ratio of vanadocene compound/oxygen ($Cp_2VX_2/O_2$) is preferably about 0.05 to about 2, more preferably about 0.1 to about 1, and the molar ratio of vanadocene compound/water ($Cp_2VX_2/H_2O$) is preferably about 0.1 to about 4, more preferably about 0.2 to about 2.

After completion of chlorination of the vanadocene compound($Cp_2VX_2$), usually the reaction solvent may be evaporated to dryness. By dissolving the resulting product, $CpVOCl_2$ or $CpVCl_3$, in a solvent, concentrating the solution, cooling the concentrate, and carrying out recrystallization, $CpVOCl_2$ or $CpVCl_3$ of high purity can be obtained. The recrystallization can remove the impurities such as alkali metal salt (MX). Solvents useful for dissolving $CpVOCl_2$ or $CpVCl_3$ are, for example, benzene, toluene, xylene and like hydrocarbons, chloroform, methylene chloride and like halogenated hydrocarbons.

EXAMPLES

The present invention will be described in more detail with reference to the following examples and test examples to which, however, the invention is not limited.

Example 1

(a) Production of Vanadocene Compound

Vanadium tetrachloride (2.3 kg) was dissolved at −10° C. in 20 liters of tetrahydrofuran. While maintaining the solution at −10° C., 27 liters of a solution of ($C_5H_5$)Na in tetrahydrofuran (conc. 0.88 mole/liter) was added dropwise over 4 hours. Solid was increasingly precipitated as ($C_5H_5$)Na was added dropwise. While stirring the resulting suspension, the temperature was elevated to 50° C. over 16 hours. While maintaining the temperature at 50° C., tetrahydrofuran was evaporated under reduced pressure and the residue was vacuum-dried for 3 hours, giving 5.1 kg of vanadocene compound as grayish-green solid. Analysis demonstrated that the solid contained 2.27 moles/kg of $(C_5H_5)_2VCl_2$.

(b) Chlorination 300 g of the obtained vanadocene compound was suspended in 2 liters of chloroform and the suspension was heated to 50° C. Chlorine gas was introduced (gas flow rate: 3.6 liters/hr), and simultaneously 7.5 milliliters of water was continuously added over 9 hours to conduct chlorination. While maintaining the temperature at 50° C., chloroform was evaporated under reduced pressure. The dry solid was washed three times with 1 liter of hexane. While the temperature of the residue was maintained at 50° C., the residue was washed twice with 1 liter of toluene. The toluene filtrates were combined and concentrated. Recrystallization gave 83 g (yield 60%) of $(C_5H_5)VOCl_2$.

Example 2
(a) Production of Vanadocene Compound

The vanadocene compound, $(C_5H_5)_2VCl_2$, was prepared in the same manner as in Example 1(a).

(b) Chlorination 150 g of the obtained vanadocene compound was suspended in 1 liter of chloroform and the suspension was heated to 50° C. Chlorine gas (gas flow 2 liters/hr) and oxygen gas (gas flow 0.6 liter/hr) were continuously supplied for 8 hours to conduct chlorination. After chlorination, the same work-up procedure as done in Example 1(b) was carried out, giving 40 g of $(C_5H_5)VOCl_2$ (yield 58%).

Example 3

The same procedure as in Example 1 was conducted except that hexane was used as the solvent in the chlorination reaction, giving $(C_5H_5)VOCl_2$.

Example 4
(a) Production of Vanadocene Compound

Vanadium tetrachloride (38 g) was dissolved in 400 milliliters of tetrahydrofuran cooled to −20° C. The temperature of the solution rose to −10° C. While retaining the temperature of the solution at −10° C., 440 milliliters of a tetrahydrofuran solution of $(C_5H_4CH_3)Li$ (concentration 0.92 mole/liter) was added dropwise over 3 hours. The temperature of the obtained suspension was elevated to room temperature over 24 hours while it was stirred. The tetrahydrofuran was evaporated under reduced pressure while retaining the temperature at 50° C. The residue was vacuum-dried for 3 hours, thereby giving a vanadocene compound, $(C_5H_4 CH_3)_2VCl_2$, as a dry solid.

(b) Chlorination 400 milliliters of chloroform was added to the dry solid of the vanadocene compound to give a suspension. While maintaining the temperature at 50° C., 2.2 milliliters of water was continuously added over 9 hours simultaneously with introduction of chlorine gas (gas flow rate: 0.95 liter/hr) to conduct chlorination. While maintaining the temperature at 50° C. after completion of chlorination reaction, the chloroform was evaporated under reduced pressure. The dry solid was washed twice with 200 milliliters of hexane. While the temperature of the residue was maintained at 50° C., the residue was washed twice with 500 milliliters of toluene. The toluene filtrates were combined and concentrated. Recrystallization gave 19 g (yield 44%) of $(C_5H_4CH_3)VOCl_2$.

Example 5
(a) Production of Vanadocene Compound

The vanadocene compound, $(C_5H_5)_2VCl_2$, was prepared in the same manner as in Example 1, (a).

(b) Chlorination 150 g of the obtained vanadocene compound was suspended in 1 liter of chloroform. Then the suspension was heated to 50° C. Chlorine gas (gas flow rate: 1.1 liters/hr) was continuously supplied for 9 hours to conduct chlorination reaction. While maintaining the temperature at 50° C., the chloroform was evaporated under reduced pressure. The dry solid (final product) was washed twice with 1 liter of hexane. While the temperature of the residue was maintained at 50° C., the residue was washed three times with 1 liter of toluene. The toluene filtrates were combined and concentrated. Recrystallization gave 39 g (yield 52%) of $(C_5H_5)VCl_3$.

Comparative Example 1

100 g of $(C_5H_5)_2VCl_2$ was suspended in 300 milliliters of chloroform. The suspension was cooled to 0° C. 300 milliliters of $SOCl_2$ as a chlorinating agent was added to the suspension. Thereby the temperature of the solution rose to 15° C. While maintaining the temperature at 30° C., oxygen (gas flow 0.6 liter/hr) was continuously supplied for 9 hours. After completion of chlorination, the chloroform and $SOCl_2$ were evaporated under reduced pressure while maintaining the temperature at 50° C. After washing the dry solid (final product) with hexane, it was washed three times with 0.5 liter of toluene. The toluene filtrates were combined and concentrated. Recrystallization gave 17 g of $(C_5H_5)VOCl_2$ (yield 21%).

Comparative Example 2

600 milliliters of $SOCl_2$ was cooled to 0° C. and 100 g of $(C_5H_5)_2VCl_2$ was added to obtain a suspension. Thereby the temperature of the suspension rose to 10° C. While maintaining the temperature at 30° C., chlorination reaction was conducted for 9 hours. After completion of chlorination reaction, the chloroform and $SOCl_2$ were evaporated under reduced pressure while maintaining the temperature at 50° C. After washing the final product (solid evaporated to dryness) with hexane, the solid was washed three times with 0.5 liter of toluene. The toluene filtrates were combined and concentrated. Recrystallization gave 16 g of $(C_5H_5)VCl_3$ (yield 18%).

The half-vanadocene compounds prepared in Examples 1 to 5 were found to have a purity of 99% or higher according to titrimetric analysis. The half-vanadocene compounds of Examples 1 to 5 were produced in a yield of 44 to 60%, which were higher than yields of about 20% in Comparative Examples 1 and 2 illustrative of the results of prior art processes. This means that according to the process of the present invention, a half-vanadocene compounds can be produced with a high purity in a high yield.

What is claimed is:

1. A process for preparing a half-vanadocene compound, the process comprising reacting chlorine gas with a vanadocene compound represented by the formula (1) in the presence of at least one member selected from the group consisting of oxygen and water, $$Cp_2VX_2 \qquad (1)$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl, and the two Cp groups may be the same or different, X represents fluorine, chlorine, bromine or iodine and the two X atoms may be the same or different.

2. A process for preparing a half-vanadocene compound according to claim 1, wherein Cp represents cyclopentadienyl; cyclopentadienyl having 1 to 5 substituents selected from the group consisting of hydrocarbon groups having 1 to 20 carbon atoms and silicon-containing hydrocarbon groups having 1 to 20 carbon atoms; indenyl; indenyl having 1 to 6 substituents selected from the group consisting of hydrocarbon groups having 1 to 20 carbon atoms and silicon-containing hydrocarbon groups having 1 to 20 carbon atoms; fluorenyl; fluorenyl having 1 to 8 substituents selected from the group consisting of hydrocarbon groups having 1 to 20 carbon atoms and silicon-containing hydrocarbon groups having 1 to 20 carbon atoms; benzoindenyl;

benzoindenyl having 1 to 8 substituents selected from the group consisting of hydrocarbon groups having 1 to 20 carbon atoms and silicon-containing hydrocarbon groups having 1 to 20 carbon atoms; azulenyl; or azulenyl having 1 to 7 substituents selected from the group consisting of hydrocarbon groups having 1 to 20 carbon atoms and silicon-containing hydrocarbon groups having 1 to 20 carbon atoms, and the two $C_p$ groups may be the same or different.

3. A process for preparing a half-vanadocene compound according to claim 1, wherein Cp represents cyclopentadienyl; cyclopentadienyl having 1 to 5 substituents selected from the group consisting of methyl, ethyl, n-propyl, iso-propyl, n-butyl, iso-butyl, sec-butyl, t-butyl and phenyl; indenyl; indenyl having 1 to 6 substituents selected from the group consisting of methyl, ethyl, n-propyl, iso-propyl, n-butyl, iso-butyl, sec-butyl, t-butyl and phenyl; fluorenyl; fluorenyl having 1 to 8 substituents selected from the group consisting of methyl, ethyl, n-propyl, iso-propyl, n-butyl, iso-butyl, sec-butyl, t-butyl and phenyl; benzoindenyl; benzoindenyl having 1 to 8 substituents selected from the group consisting of methyl, ethyl, n-propyl, iso-propyl, n-butyl, iso-butyl, sec-butyl, t-butyl and phenyl; benzoindenyl; benzoindenyl having 1 to 8 substituents selected from the group consisting of methyl, ethyl, n-propyl, iso-propyl, n-butyl, iso-butyl, sec-butyl, t-butyl and phenyl; azulenyl; or azulenyl having 1 to 7 substituents selected from the group consisting of methyl, ethyl, n-propyl, iso-propyl, n-butyl, iso-butyl, sec-butyl, t-butyl and phenyl, and the two Cp groups may be the same or different.

4. The process for preparing a half-vanadocene compound according to claim 1, wherein the compound represented by the formula (1) is selected from the group consisting of $(C_5H_5)_2VF_2$, $(C_5H_5)_2VCl_2$, $(C_5H_5)_2VBr_2$, $(C_5H_5)_2VI_2$, $(CH_3C_5H_4)_2VF_2$, $(CH_3C_5H_4)_2VCl_2$, $(CH_3C_5H_4)_2VBr_2$, $(CH_3C_5H_4)_2VI_2$, $[1,2-(CH_3)_2C_5H_3]_2VF_2$, $[1,2-(CH_3)_2C_5H_3]_2VCl_2$, $[1,2-(CH_3)_2C_5H_3]_2VBr_2$, $[1,2-(CH_3)_2C_5H_3]_2VI_2$, $[1,3-(CH_3)_2C_5H_3]_2VF_2$, $[1,3-(CH_3)_2C_5H_3]_2VCl_2$, $[1,3-(CH_3)_2C_5H_3]_2VBr_2$, $[1,3-(CH_3)_2C_5H_3]_2VI_2$, $[1,2,3-(CH_3)_3C_5H_2]_2VF_2$, $[1,2,3-(CH_3)_3C_5H_2]_2VCl_2$, $[1,2,3-(CH_3)_3C_5H_2]_2VBr_2$, $[1,2,3-(CH_3)_3C_5H_2]_2VI_2$, $[1,2,4-(CH_3)_3C_5H_2]_2VF_2$, $[1,2,4-(CH_3)_3C_5H_2]_2VCl_2$, $[1,2,4-(CH_3)_3C_5H_2]_2VBr_2$, $[1,2,4-(CH_3)_3C_5H_2]_2VI_2$, $[(CH_3)_4C_5H]_2VF_2$, $[(CH_3)_4C_5H]_2VCl_2$, $[(CH_3)_4C_5H]_2VBr_2$, $[(CH_3)_4C_5H]_2VI_2$, $[(CH_3)_5C_5]_2VF_2$, $[(CH_3)_5C_5]_2VCl_2$, $[(CH_3)_5C_5]_2VBr_2$, $[(CH_3)_5C_5]_2VI_2$, $(1-CH_3-2-C_2H_5C_5H_3)_2VF_2$, $(1-CH_3-2-C_2H_5C_5H_3)_2VCl_2$, $(1-CH_3-2-C_2H_5C_5H_3)_2VBr_2$, $(1-CH_3-2-C_2H_5C_5H_3)_2VI_2$, $1-CH_3-3-C_2H_5C_5H_3)_2VF_2$, $(1-CH_3-3-C_2H_5C_5H_3)_2VCl_2$, $(1-CH_3-3-C_2H_5C_5H_3)_2VBr_2$, $(1-CH_3-3-C_2H_5C_5H_3)_2VI_2$, $(1-CH_3-2-n-C_3H_7C_5H_3)_2VF_2$, $(1-CH_3-2-n-C_3H_7C_5H_3)_2VCl_2$, $(1-CH_3-2-n-C_3H_7C_5H_3)_{3\ 2}VBr_2$, $(1-CH_3-2-n-C_3H_7C_5H_3)_2VI_2$, $(1-CH_3-2-iso-C_3H_7C_5H_3)_2VF_2$, $(1-CH_3-2-iso-C_3H_7C_5H_3)_2VCl_2$, $(1-CH_3-2-iso-C_3H_7C_5H_3)_2VBr_2$, $(1-CH_3-2-iso-C_3H_7C_5H_3)_2VI_2$, $(1-CH_3-3-n-C_3H_7C_5H_3)_2VF_2$, $(1-CH_3-3-n-C_3H_7C_5H_3)_{\ 2}VCl_2$, $(1-CH_3-3-n-C_3H_7C_5H_3)_2VBr_2$, $(1-CH_3-3-n-C_3H_7C_5H_3)_2VI_2$, $(1-CH_3-3-iso-C_3H_7C_5H_3)_2VF_2$, $(1-CH_3-3-iso-C_3H_7C_5H_3)_2Cl_2$, $(1-CH_33-iso-C_3H_7C_5H_3)_2VBr_2$, $(1-CH_3-iso-C_3H_7C_5H_3)_2VI_2$, $(C_2H_5C_5H_4)_2VF_2$, $(C_2H_5C_5H_4)_2VCl_2$, $(C_2H_5C_{54})_2VBr_2$, $(C_2H_5C_5H_4)_2VI_2$, $[1,2-(C_2H_5)_2C_5H_3]_2VF_2$, $[1,2-(C_2H_5)_2C_5H_3]_2VCl_2$, $[1,2-(C_2H_5)_2C_5H_3]_2VBr_2$, $[1,2-(C_2H_5)_2C_5H_3]_2VI_2$, $[1,3-(C_2H_5)_2C_5H_3]_2VF_2$, $[1,3-(C_2H_5)_2C_5H_3]_2VCl_2$, $[1,3-(C_2H_5)_2C_5H_3]_2VBr_2$, $[1,3-(C_2H_5)_2\ C_5H_3]_2VI_2$, $[1,2-(n-C_3H_7)_2C_5H_3]_{2,\ }VF_2$, $[1,2-(n-C_3H_7)_2C_5H_3]_2VCl_2$, $[1,2-(n-C_3H_7)_2C_5H_3]_2VBr_2$, $[1,2-(n-C_3H_7)_2C_5H_3]_2VI_2$, $[1,3-(n-C_3H_7)_2C_5H_3]_2VF_2$, $[1,3-(n-C_3H_7)_2C_5H_3]_2VCl_2$, $[1,3-(n-C_3H_7)_2C_5H_3]_2VBr_2$, $[1,3-(n-C_3H_7)_2C_5H_3]_2VI_2$, $[1,2-(iso-C_3H_7)_2C_5H_3]_2VF_2$, $[1,2-(iso-C_3H_7)_2C_5H_3]_2VCl_2$, $[1,2-(iso-C_3H_7)_2C_5H_3]_2VBr_2$, $[1,2-(iso-C_3H_7)_2C_5H_3]_2VI_2$, $[1,3-(iso-C_3H_7)_2C_5H_3]_2VF_2$, $[1,3-(iso-C_3H_7)_2C_5H_3]_2VCl_2$, $[1,3-(iso-C_3H_7)_2C_5H_3]_2VBr_2$, $[1,3-(iso-C_3H_7)_2C_5H_3]_2VI_2$, $[1,2-(n-C_4H_9)_2C_5H_3]_2VF_2$, $[1,2-(n-C_4H_9)_2C_5H_3]_2VCl_2$, $1,2-(n-C_4H_9)_2C_5H_3]_2VBr_2$, $[1,2-(n-C_4H_9)_2C_5H_3]_2VI_2$, $[1,3-(n-C_4H_9)_2C_5H_3]_2VF_2$, $[1,3-(n-C_4H_9)_2C_5H_3]_2VCl_2$, $[1,3-(n-C_4H_9)_2C_5H_3]_2VBr_2$, $[1,3-(n-C_4H_9)_2C_5H_3]_2VBr_2$, $[1,3-(t-C_4H_9)_2C_5H_3]_2VI_2$, $(n-C_5H_{11}C_5H_4)_2VF_2$, $(n-C_5H_{11}C_5H_4)_2VCl_2$, $(n-C_5H_{11}C_5H_4)_2VBr_2$, $(n-C_5H_{11}C_5H_4)_2VI_2$, $(n-C_6H_{13}C_5H_4)_2\ VF_2$, $(n-C_6H_{13}C_5H_4)_2VCl_2$, $(n-C_6H_{13}C_5H_4)_2VBr_2$, $(n-C_6H_{13}C_5H_4)_2VI_2$, $(n-C_8H_{17}C_5H_4)_2\ VF_2$, $(n-C_8H_{17}C_5H_4)_2VCl_2$, $(n-C_8H_{17}C_5H_4)_2VBr_2$, $(n-C_8H_{17}C_5H_4)_2VI_2$, $(C_6H_5C_5H_4)_2VF_2$, $(C_6H_5C_5H_4)_2VCl_2$, $(C_6H_5C_5H_4)_2VBr_2$, $(C_6H_5C_5H_4)_2VI_2$, $(C_6H_5CH_2C_5H_4)_2VF_2$, $(C_6H_5CH_2C_5H_4)_2VCl_2$, $(C_6H_5CH_2C_5H_4)_2VBr_2$, $(C_6H_5CH_2C_5H_4)_2VI_2$, $[(CH_3)_3SiC_5H_4]_2$, $VF_2$, $[(CH_3)_3SiC_5H_4]_2VCl_2$, $[(CH_3)_3SiC_5H_4]_2VBr_2$, $[(CH_3)_3SiC_5H_4]_2VI_2$, $\{1,3-[(CH_3)_3Si]_2C_5H_3\}_2VF_2$, $\{1,3-[(CH_3)_3Si]_2C_5H_3\}_2VCl_2$, $\{1,3-[(CH_3)_3Si]_2C_5H_3\}_2VBr_2$, $\{1,3-[(CH_3)_3Si]_2C_5H_3\}_2VI_2$, $[(CH_3)_9Si(CH_3)C_5H_3]_2VF_2$, $[1-(CH_3)_3Si-3-CH_3C_5H_3]_2VCl_2$, $[1-(CH_3)_3Si-3-CH_3C_5H_3]_2VBr_2$, $[1-(CH_3)_3Si-3-CH_3C_5H_3]_2VI_2$, $\{1,3-[(CH_3)_3Si]_2-4-CH_3C_5H_2\}_2VF_2$, $\{1,3-[(CH_3)_3Si]_2-4-CH_3C_5H_2\}_2VCl_2$, $\{1,3-[(CH_3)_3Si]_2-4-CH_3C_5H_2\}_2VBr_2$, $\{1,3-[(CH_3)_3Si]_2-4-CH_3C_5H_2\}_2VI_2$, $Ind_2VF_2$, $Ind_2VCl_2$, $Ind_2VBr_2$, $Ind_2VI_2$, $(2-CH_3Ind)_2VF_2$, $(2-CH_3Ind),_{\ 2}VCl_2$, $(2-CH_3Ind)_2VBr_2$, $(2-CH_3Ind)_2VI_2$, $(2-C_2H_5Ind)_2VF_2$, $(2-C_2H_5Ind)_2VCl_2$, $(2-C_2H_5Ind)_2VBr_2$, $(2-C_2H_5Ind)_2VI_2$, $(2-n-C_3H_7Ind)_2VF_2$, $(2-n-C_3H_7Ind)_2VCl_2$, $(2-n-C_3H_7Ind)_2VBr_2$, $(2-n-C_3H_7Ind),_{\ 2}VI_2$, $(2-iso-C_3H_7Ind)_2VF_2$, $(2-iso-C_3H_7Ind)_2VCl_2$, $(2-iso-C_3H_7Ind)_2VBr_2$, $(2-iso-C_3H_7Ind)_2VI_2$, $(2-n-C_4H_9Ind)_2VF_2$, $(2-n-C_4H_9Ind)_2VCl_2$, $(2-n-C_4H_9Ind)_2VBr_2$, $(2-n-C_4H_9Ind)_2VI_2$, $(2-t-C_4H_9Ind)_2VF_2$, $(2-t-C_4H_9Ind)_2VCl_2$, $(2-t-C_4H_9Ind)_2VBr_2$, $(2-t-C_4H_9Ind)_2VI_2$, $[2-(CH_3)_3SiInd)]_2VF_2$, $[2-(CH_3)_3SiInd)]_2VCl_2$, $[2-(CH_3)_3SiInd)]_2VBr_2$, $[2-(CH_3)_3SiInd)]_2VI_2$, $[2,4-(CH_3)_2Ind)]_2VF_2$, $[2,4-(CH_3)_2Ind)]_2VCl_2$, $[2,4-(CH_3)_2Ind)]_2VBr_2$, $[2,4-(CH_3)_2Ind)]_2VI_2$, $[2-(CH_3)-4-C_6H_5Ind)]_2VF_2$, $[2-CH_3-4-C_6H_5Ind)]_2VCl_2$, $[2-CH_3)-4-C_6H_5Ind)]_2VBr_2$, $[2-(CH_3)-4-C_6H_5Ind)]_2VI_2$, $(H_4Ind)_2VF_2$, $(H_4Ind)_2VCl_2$, $(H_4Ind)_2VBr_2$, $(H_4Ind)_2VI_2$, $Flu_2VF_2$, $Flu_2VCl_2$, $Flu_2VBr_2$, $Flu_2VI_2$, $(9-CH_3Flu)_2VF_2$, $(9-CH_3Flu)_2VCl_2$, $(9-CH_3Flu)_2VBr_2$, $(9-CH_3Flu)_2VI_2$, $(9-C_2H_5Flu)_2VF_2$, $(9-C_2H_5Flu)_2VCl_2$, $(9-C_2H_5Flu)_2VBr_2$, $(9-C_2H_5Flu)_2VI_2$, $(9-n-C_3H_7Flu)_2VF_2$, $(9-n-C_3H_7Flu)_2VCl_2$, $(9-n-C_3H_7Flu)_2VBr_2$, $(9-n-C_3H_7Flu)_2VI_2$, $(9-iso-C_3H_7Flu)_2VF_2$, $(9-iso-C_3H_7Flu)_2VCl_2$, $(9-iso-C_3H_7Flu)_2VBr_2$, $(9-iso-C_3H_7Flu)_2VI_2$, $(9-n-C_4H_9Flu)_2VF_2$, $(9-n-C_4H_9Flu)_2VCl_2$, $(9-n-C_4H_9Flu)_2VBr_2$, $(9-n-C_4H_9Flu)_2VI_2$, $[1,9-(CH_3)_2Flu)_2VF_2$, $[1,9-(CH_3)_2Flu)_2VCl_2$, $[1,9-(CH_3)_2Flu]_2VBr_2$, $[1,9-(CH_3)_2Flu]_2VI_2$, $(H_8Flu)_2VF_2$, $(H_8Flu)_2VCl_2$, $(H_8Flu)_2VBr_2$, $(H_8Flu)_2VI_2$, $(Bind_2VF_2)$, $(Bind_2VCl_2)$, $(Bind_2VBr_2)$, $(Bind_2VI_2)$, $(2-CH_3Bind)_2VF_2$, $(2-CH_3Bind)_2VCl_2$, $(2-CH_3Bind)_2VBr_2$, $(2-CH_3Bind)_2VI_2$, $(2-C_2H_5Bind)_2VF_2$, $(2-C_2H_5Bind)_2VCl_2$, $(2-C_2H_5Bind)_2VBr_2$, $(2-C_2H_5Bind)_2VI_2$, $(2-n-C_3H_7Bind)_2VF_2$, $(2-n-C_3H_7Bind)_2VCl_2$, $(2-n-C_3H_7Bind)_2VBr_2$, $(2-n-C_3H_7Bind)_2VI_2$, $(2-iso-C_3H_7Bind)_2VF_2$, $(2-iso-C_3H_7Bind)_2VCl_2$, $(2-iso-C_3H_7Bind)_2VBr_2$, $(2-iso-C_3H_7Bind)_2VI_2$, $(2-n-C_4H_9Bind)_2VF_2$, $(2-n-C_4H_9Bind)_2VCl_2$, $(2-n-C_4H_9Bind)_2VBr_2$, $(2-n-C_4H_9Bind)_2VI_2$, $(2-t-C_4H_9Bind)_2VF_2$, $(2-t-C_4H_9Bind)_2VCl_2$, $(2-t-C_4H_9Bind)_2VBr_2$, $(2-t-C_4H_9Bind)_2VI_2$, $Azu_2VF_2$, $Azu_2VCl_2$, $Azu_2VBr_2$, $Azu_2VI_2$, $(2-CH_3Azu)_2\ VF_2$, $(2-CH_3Azu)_2VCl_2$, $(2-CH_3AZU)_2VBr_2$, $(2-CH_3Azu)_2VI_2$, $(2-C_2H_5Azu)_2VF_2$, $(2-C_2H_5Azu)_2VCl_2$, $(2-C_2H_5Azu)_2VBr_2$, $(2-C_2H_5Azu)_2VI_2$, $(2-n-C_3H_7Azu)_2$ $VF_2$, $(2\text{-}n\text{-}C_3H_7Azu)_2VCl_2$, $(2\text{-}n\text{-}C_3H_7Azu)_2VBr_2$, $(2\text{-}n\text{-}C_3H_7Azu)_2VI_2$, $(2\text{-}iso\text{-}C_3H_7Azu)_2VF_2$, $(2\text{-}iso\text{-}C_3H_7Azu)_2VCl_2$, $(2\text{-}iso\text{-}C_3H_7Azu)_2VBr_2$, $(2\text{-}iso\text{-}C_3H_7Azu)_2VI_2$, $(4,8\text{-}(CH_3)_2Azu)_2VF_2$, $(4,8\text{-}(CH_3)_2Azu)_2VCl_2$, $(4,8\text{-}(CH_3)_2Azu)_2VBr_2$, $(4,8\text{-}(CH_3)_2Azu)_2VI_2$, $(2,4,8\text{-}(CH_3)_3Azu)_2VF_2$, $(2,4,8\text{-}(CH_3)_3Azu)_2VCl_2$, $(2,4,8\text{-}(CH_3)_3Azu)_2Br_2$, $(2,4,8\text{-}(CH_3)_3Azu)_2VI_2$, $[2\text{-}iso\text{-}C_3H_7\text{-}4,8\text{-}(CH_3)_2Azu]_2VF_2$, $[2\text{-}iso\text{-}C_3H_7\text{-}4,8\text{-}(CH_3)_2Azu]_2VCl_2$, $[2\text{-}iso\text{-}C_3H_7\text{-}4,8\text{-}(CH_3)_2Azu]_2VBr_2$, and $[2\text{-}iso\text{-}C_3H_7\text{-}4,8\text{-}(CH_3)_2Azu]_2VI_2$, wherein Ind represents indenyl, Flu represents fluorenyl, Bind represents benzoindenyl, Azu represents azylenyl, $H_4Ind$ represents the following group (6).

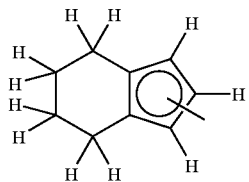
(6)

and $H_8Flu$ represents the following group (7).

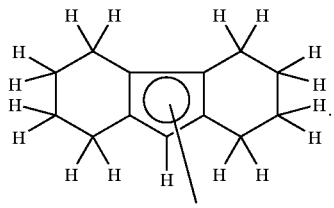
(7)

5. The process for preparing a half-vanadocene compound according to claim 1, wherein the half-vanadocene compound to be obtained is a compound represented by the formula (3)

$$CpVOCl_2 \qquad (3)$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl.

6. A process for preparing a half-vanadocene compound, the process comprising reacting chlorine gas with a vanadocene compound represented by the formula (1) in the presence of oxygen and water, $$Cp_2VX_2 \qquad (1)$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl, and the two Cp groups may be the same or different, X represents fluorine, chlorine, bromine or iodine and the two X atoms may be the same or different.

7. The process for preparing a half-vanadocene compound according to claim 6, wherein the half-vanadocene compound to be obtained is a compound represented by the formula (3)

$$CpVOCl_2 \qquad (1)$$

wherein Cp represents cyclopentadienyl, substituted cyclopentadienyl, indenyl, substituted indenyl, fluorenyl, substituted fluorenyl, benzoindenyl, substituted benzoindenyl, azulenyl or substituted azulenyl.

* * * * *

UNITED STATES PATENT AND TRADEMARK OFFICE
CERTIFICATE OF CORRECTION

PATENT NO.      : 6,849,753 B2
APPLICATION NO. : 10/298624
DATED           : February 1, 2005
INVENTOR(S)     : Tadanao Kohara and Tomoya Kubo It is certified that error appears in the above-identified patent and that said Letters Patent is hereby corrected as shown below:

At column 3, line 30, please delete "VBR$_2$" and insert therefor, --VBr$_2$--.

At column 4, line 7, please delete "$_{\{1,3}$-[ (CH$_3$)" and insert therefor, --{1,3-[ (CH$_3$)--.

At column 4, line 7, please delete "$_{\{1,3}$-" and insert therefor, --{1,3- --.

At column 4, line 8, please delete "$_{\{1,3}$-[ (CH$_3$) " and insert therefor, --{1,3-[ (CH$_3$)--.

At column 4, line 9, please delete "(*CH$_3$*)" and insert therefor, --(CH$_3$)--.

At column 4, line 14, please delete " -4-CH$_3$C$_5$- " and insert therefor, -- -4-CH$_3$C$_5$--.

At column 4, line 17, please delete "VBrF$_2$" and insert therefor, --VBr$_2$--.

At column 4, line 30, please delete "(H$_4$Ind)2VF$_2$" and insert therefor, --(H$_4$Ind)$_2$VF$_2$--.

At column 4, line 35, before (9-n-C$_3$H$_7$Flu)$_2$, please delete "VCl$_2$," and insert therefor,

--VI$_2$--

At column 4, line 43, please delete "Bind2VCl$_2$" and insert therefor, --Bind$_2$VCl$_2$--.

At column 4, line 53, please delete "(2-1-C$_4$H$_9$" and insert therefor, --(2-t-C$_4$H$_9$--.

At column 4, line 55, please delete "Azu2VCl$_2$" and insert therefor, --azU$_2$VCl$_2$--.

At column 4, line 61, please delete "C$_3$H$_7$AZU" and insert therefor, --C$_3$H$_7$Azu--.

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

At column 4, line 62, please delete "$C_3H_7Azu)_{2VI2}$" and insert therefor,

--$C_3H_7Azu)_2VI_2$--.

At column 5, lines 7-13, please delete

"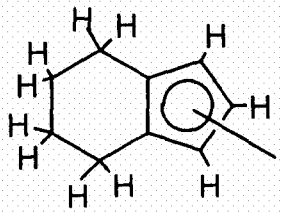 (6)"

and insert therefor,

--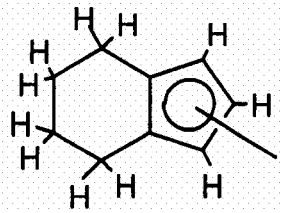 (6)--.

At column 5, lines 18-26, please delete

"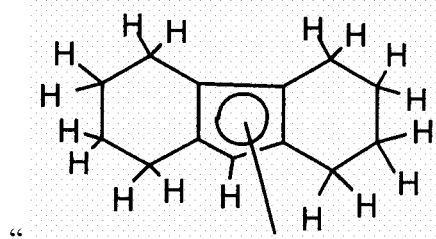 (7)"

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

and insert therefor,

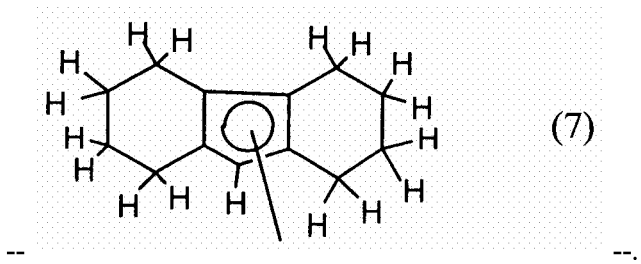

--      (7)      --.

At column 5, lines 53-55, please delete

"CPVCl$_3$     (2)"

and insert therefor,

--CpVCl$_3$     (2)--.

At column 7, line 4, please delete "Vanadocene compound" and insert therefor,

--<u>Vanadocene compound</u>--.

At column 7, line 24, before alkyl groups, please add -- - --

At column 7, line 29, before aralkyl groups, please add -- - --

At column 7, line 31, before aryl groups, please add -- - --

At column 8, line 48, after VF$_2$, please delete "[1,3- (CH$_3$) $_3$C$_5$H$_2$] $_2$" and insert therefor, -- [1,2,3- (CH$_3$) $_3$C$_5$H$_2$] $_2$--.

At column 8, line 54, please delete "(1-CH$_3$-2-C$_2$H$_5$C$_5$H$_3$)$_2$VI$_2$" and insert therefor, --[(CH$_3$) $_5$C$_5$] $_2$VI$_2$,--.

At column 8, line 59, please delete " 2-n-C$_3$H$_7$C$_5$H$_{3)2}$VCl$_2$, " and insert therefor, --2-n-C$_3$H$_7$C$_5$H$_3$)$_2$VCl$_2$,--.

At column 8, line 60, after VBr$_2$, please delete "(1-CH$_3$-2-n-C$_3$H$_7$C$_5$H$_3$) $_2$VBr$_2$,"

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

At column 8, line 66, please delete "(1-$CH_3$-iso-" and insert therefor, --(1-$CH_3$-3-iso--.

At column 9, line 1, please delete "$V1_2$" and insert therefor, --$VI_2$--.

At column 9, line 2, after $VCl_2$, please add --,--.

At column 9, line 2, after $VBr_2$, please add --,--.

At column 9, line 19, please delete "[1,3(t-$C_4H_9$) $_2$" and insert therefor, --[1,3-(t-$C_4H_9$) $_2$--.

At column 9, line 21, please delete "(n-$C_5H_4$) $_2$" and insert therefor, --(n-$C_5H_{11}C_5H_4$) $_2$--.

At column 9, line 27, please delete "($C_6H_5C_5H_4$) $_2$" and insert therefor,
--($C_6H_5CH_2C_5H_4$) $_2$--.

At column 9, line 31, please delete "$C_5H_3\}_2$" and insert therefor, --$C_5H_3\}_2$--.

At column 9, line 32, please delete "$C_5H_3\}_2VI_2$" and insert therefor, --$C_5H_3\}_2VI_2$--.

At column 9, line 33, after $VF_2$, please add --,--.

At column 9, line 41, after $VCl_2$, please delete "(2-n-$C_3H_7$Ind)$_2$"

At column 9, line 42, please delete "$VCl_2$ ,".

At column 9, line 48, after $VBr_2$, please add --,--.

At column 10, line 23, after group, please add --(6)--.

At column 10, line 33, after group, please delete ".".

At column 10, line 50, please delete "[ ($CH_3$) $_4C_5$] $_2$" and insert therefor,
--[ ($CH_3$) $_4C_5H$] $_2$--.

At column 11, line 10, please delete "Process for Preparing Vanadocene Compound ( $Cp_2VX_2$ )" and insert therefor,

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

--Process for Preparing Vanadocene Compound ($Cp_2VX_2$)--.
At column 11, lines 15-17, please delete

"
 (4)    (5)    (1)"

and insert therefore,

--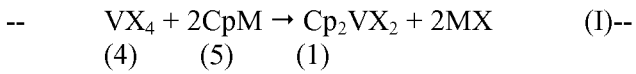
 (4)    (5)    (1)--

At column 13, line 57, after 100°C please delete "."

At columne 13, line 5, please delete "Chlorination of the Vanadocene Compound ($Cp_2VX_2$)" and insert therefor, --Chlorination of the Vanadocene Compound ($Cp_2VX_2$)--

At column 14, line 7, after 150°C please delete "."

At column 14, line 51, after 50°C please delete "."

At column 14, line 52, after 50°C please delete "."

At column 14, line 64, after 50°C please delete "."

At column 14, line 67, after 50°C please delete "."

At column 15, line 26, after -10°C please delete "."

At column 15, line 38, after 50°C please delete "."

At column 15, line 42, after 50°C please delete "."

At column 15, line 45, after 50°C please delete "."

At column 15, line 58, after 50°C please delete "."

At column 15, line 60, after 50°C please delete "."

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

At column 16, line 6, after 30°C please delete ".".

At column 16, line 21, after 30°C please delete ".".

At column 16, lines 45-47, please delete "$CP_2VX_2$" and insert therefor, --$Cp_2VX_2$--.

At column 17, line 8, please delete "$C_P$" and insert therefor, --Cp--.

At column 17, lines 23-26, after phenyl, in line 23, before azulenyl, in line 26, please delete "benzoindenyl; benzoindenyl having 1 to 8 substituents selected from the group consisting of methyl, ethyl, n-propyl, iso-propyl, n-butyl, iso-butyl, sec-butyl, t-butyl, and phenyl;"

At column 17, line 34, please delete "$(C_5H_5)_2$," and insert therefor, --$(C_5H_5)_2$--.

At column 17, line 34, please delete "$VCl_2$" and insert therefor, --$VCl_2$--.

At column 17, line 37, please delete "$[1,2\text{-}CH_{32}C_5H_3]_2$" and insert therefor, -- $[1,2\text{-}(CH_3)_2C_5H_3]_2$ --.

At column 17, line 47, please delete "$C_2H_5C_5H_{32}\ VCl_2$," and insert therefor, -- $C_2H_5C_5H_3)_2\ VCl_2$,--.

At column 17, line 47, please delete "$(1\text{-}CH_3\text{-}C_2H_5C_5H_3)_2$" and insert therefor, --$(1\text{-}CH_3\text{-}2\text{-}C_2H_5C_5H_3)_2$--.

At column 17, line 48, please delete "$1\text{-}CH_3\text{-}3\text{-}C_2H_5C_5H_3)_2$" and insert therefor, --$(1\text{-}CH_3\text{-}3\text{-}C_2H_5C_5H_3)_2$--.

At column 17, line 51, please delete "$(1\text{-}CH_3\text{-}2\text{-}n\text{-}C_3H_7C_5H_3)_{32}$" and insert therefor, --$(1\text{-}CH_3\text{-}2\text{-}n\text{-}C_3H_7C_5H_3)_2$--.

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

At column 17, line 55, please delete "$(1\text{-}CH_3\text{-}3\text{-}n\text{-}C_3H_7C_5H_3)_2 \text{ VCl}_2$" and insert therefor, --$(1\text{-}CH_3\text{-}3\text{-}n\text{-}C_3H_7C_5H_3)_2 \text{ VCl}_2$--.

At column 17, line 58, please delete "$C_3H_7C_5H_3)_2 \text{ Cl}_2$" and insert therefor, --$C_3H_7C_5H_3)_2 \text{ VCl}_2$--.

At column 17, line 58, please delete "$(1\text{-}CH_3 3\text{-}iso\text{-}C_3H_7C_5H_3)_2$" and insert therefor, --$(1\text{-}CH_3\text{-}3\text{-}iso\text{-}C_3H_7C_5H_3)_2$--.

At column 17, line 58, please delete "$(1\text{-}CH_3\text{-}$" and insert therefor, --$(1\text{-}CH_3\text{-}3$---.

At column 17, line 64, please delete "$C_5H_3)_2 \text{ VF}_2$" and insert therefor, --$C_5H_3)_2 \text{ VF}_2$--.

At column 17, line 67, please delete "$VCI_2$" and insert therefor, --$VCl_2$--.

At column 18, line 2, please delete "$VCI_2$" and insert therefor, --$VCl_2$--.

At column 18, line 4, please delete "$VCI_2$" and insert therefor, --$VCl_2$--.

At column 18, line 6, please delete "$VCI_2$" and insert therefor, --$VCl_2$--.

At column 18, line 8, please delete "$VCI_2$" and insert therefor, --$VCl_2$--.

At column 18, lines 8-9, after $VBr_2$, please delete "$[1,3\text{-}(n\text{-}C_4H_9)_2C_5H_3]_2VBr_2, [1,3\text{-}(t\text{-}C_4H_9)_2C_5H_3]_2VI_2,$" and insert therefor, --$[1,3\text{-}(n\text{-}C_4H_9)_2C_5H_3]_2VF_2, [1,3\text{-}(t\text{-}C_4H_9)_2C_5H_3]_2VCl_2, [1,3\text{-}(t\text{-}C_4H_9)_2C_5H_3]_2VBr_2, [1,3\text{-}(t\text{-}C_4H_9)_2C_5H_3]_2VBr_2, [1,3\text{-}(t\text{-}C_4H_9)_2C_5H_3]_2VI_2,$--

At column 18, line 10, please delete "$(n\text{-}C_5H_{12}C_5H_4)_2 VCI_2$" and insert therefor, --$(n\text{-}C_5H_{11}C_5H_4)_2 VCl_2$--.

At column 18, line 12, please delete "$VCI_2$" and insert therefor, --$VCl_2$--.

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

At column 18, line 14, please delete "VCI$_2$" and insert therefor, --VCl$_2$--.

At column 18, line 16, please delete "VCI$_2$" and insert therefor, --VCl$_2$--.

At column 18, line 17, please delete "VCI$_2$" and insert therefor, --VCl$_2$--.

At column 18, line 19, please delete ",VF$_2$" and insert therefor, --VF$_2$--.

At column 18, line 19, please delete "VCI$_2$" and insert therefor, --VCl$_2$--.

At column 18, line 21, please delete "VCI$_2$" and insert therefor, --VCl$_2$--.

At column 18, line 22, please delete "[(CH$_3$) $_9$Si(CH$_3$)" and insert therefor, --[(CH$_3$) $_3$Si(CH$_3$)--.

At column 18, line 23, please delete "VCI$_2$" and insert therefor, --VCl$_2$--.

At column 18, line 26, please delete "VCI$_2$" and insert therefor, --VCl$_2$--.

At column 18, line 27, please delete "VCI$_2$" and insert therefor, --VCl$_2$--.

At column 18, line 28, please delete ",$_2$VC1$_2$" and insert therefor, --VCl$_2$--.

At column 18, line 30, please delete "VCI$_2$" and insert therefor, --VCl$_2$--.

At column 18, line 32, please delete ",$_2$VI$_2$" and insert therefor, --VI$_2$--.

At column 18, line 33, please delete "VCI$_2$" and insert therefor, --VCl$_2$--.

At column 18, line 34, please delete "VCI$_2$" and insert therefor, --VCl$_2$--.

At column 18, line 36, please delete "VCI$_2$" and insert therefor, --VCl$_2$--.

At column 18, line 37, please delete "VCI$_2$" and insert therefor, --VCl$_2$--.

At column 18, line 39, please delete "VCI$_2$" and insert therefor, --VCl$_2$--.

At column 18, line 40, please delete "[2-CH$_3$-" and insert therefor, --(2-CH$_3$---.

UNITED STATES PATENT AND TRADEMARK OFFICE
CERTIFICATE OF CORRECTION

PATENT NO.       : 6,849,753 B2
APPLICATION NO.  : 10/298624
DATED            : February 1, 2005
INVENTOR(S)      : Tadanao Kohara and Tomoya Kubo It is certified that error appears in the above-identified patent and that said Letters Patent is hereby corrected as shown below:

At column 18, line 41, please delete

"-4-$C_6H_5$Ind) $]_2$VC$I_2$,[2-$CH_3$) -4-$C_6H_5$Ind) $]_2$VBr$_2$, [2-($CH_3$)-" and insert therefor, --4-$C_6H_5$Ind) $_2$VC$I_2$, (2-$CH_3$-4-$C_6H_5$Ind) $_2$VBr$_2$, (2-$CH_3$---.

At column 18, line 42, please delete "4-$C_6H_5$Ind) $]_2$V$I_2$," and insert therefor, --4-$C_6H_5$Ind) $_2$V$I_2$,--.

At column 18, line 42, please delete "VC$I_2$" and insert therefor, --VC$l_2$--.

At column 18, line 43, please delete "VC$I_2$" and insert therefor, --VC$l_2$--.

At column 18, line 45, please delete "VC$I_2$" and insert therefor, --VC$l_2$--.

At column 18, line 47, please delete "VC$I_2$" and insert therefor, --VC$l_2$--.

At column 18, line 48, please delete "VC$I_2$" and insert therefor, --VC$l_2$--.

At column 18, line 50, please delete "VC$I_2$" and insert therefor, --VC$l_2$--.

At column 18, line 51, please delete "[1,9- ($CH_3$) $_2$Flu) V$F_2$" and insert therefor, --[1,9- ($CH_3$) $_2$Flu] V$F_2$--.

At column 18, line 51, please delete "[1,9- ($CH_3$) $_2$Flu) VC$I_2$" and insert therefor, --"[1,9- ($CH_3$) $_2$Flu] VC$l_2$--.

At column 18, line 53, please delete "VC$I_2$" and insert therefor, --VC$l_2$--.

At column 18, line 53, please delete "(Bind$_2$V$F_2$ )" and insert therefor, --Bind$_2$V$F_2$--.

At column 18, line 54, please delete "(Bind$_2$VC$l_2$ )" and insert therefor, --Bind$_2$VC$l_2$--.

At column 18, line 54, please delete "(Bind$_2$VBr$_2$ )" and insert therefor, --Bind$_2$VBr$_2$--.

At column 18, line 54, please delete "(Bind$_2$V$I_2$ )" and insert therefor, --Bind$_2$V$I_2$--.

UNITED STATES PATENT AND TRADEMARK OFFICE
CERTIFICATE OF CORRECTION

PATENT NO.       : 6,849,753 B2
APPLICATION NO. : 10/298624
DATED            : February 1, 2005
INVENTOR(S)      : Tadanao Kohara and Tomoya Kubo It is certified that error appears in the above-identified patent and that said Letters Patent is hereby corrected as shown below:

At column 18, line 56, please delete "$VCI_2$" and insert therefor, --$VCl_2$--.

At column 18, line 58, please delete "$VCI_2$" and insert therefor, --$VCl_2$--.

At column 18, line 59, please delete "$VCI_2$" and insert therefor, --$VCl_2$--.

At column 18, line 61, please delete "$VCI_2$" and insert therefor, --$VCl_2$--.

At column 18, line 63, please delete "$VCI_2$" and insert therefor, --$VCl_2$--.

At column 18, line 65, please delete "$VCI_2$" and insert therefor, --$VCl_2$--.

At column 18, line 65, please delete "$(2\text{-}CH_3AZU)_2VBr_2$" and insert therefor, --$(2\text{-}CH_3Azu)_2VBr_2$--.

At column 18, line 66, please delete "$VCI_2$" and insert therefor, --$VCl_2$--.

At column 19, line 1, please delete "$VCI_2$" and insert therefor, --$VCl_2$--.

At column 19, line 4, please delete "$VCI_2$" and insert therefor, --$VCl_2$--.

At column 19, line 11, please delete "azylenyl" and insert therefor, --azulenyl--.

At column 19, lines 12-22, please delete

" 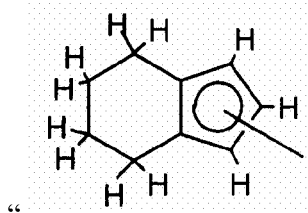 " (6)

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

and insert therefor,

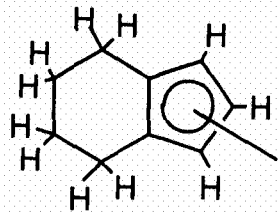  (6)

-- --.

At column 19, lines 24-33, please delete

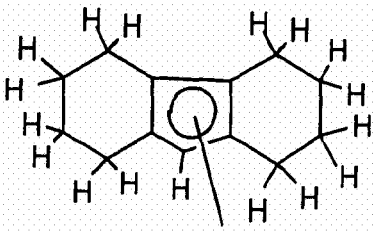  (7)

" "

and insert therefor,

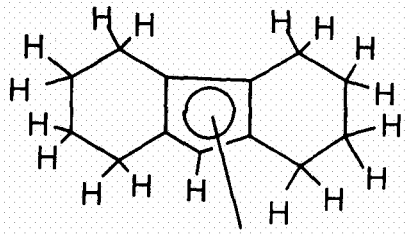  (7)

-- --

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara and Tomoya Kubo It is certified that error appears in the above-identified patent and that said Letters Patent is hereby corrected as shown below:

At column 20, lines 28-30, please delete "CpVOCl$_2$ (1)" and insert therefor, --CpVOCl$_2$ (3)--.

Signed and Sealed this

Twenty-fourth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara It is certified that error appears in the above-identified patent and that said Letters Patent is hereby corrected as shown below:

At column 4, line 55, please delete "$azU_2VCl_2$" and insert therefor, --$Azu_2VCl_2$--

At column 12, line 57, after "100°C" please delete "."

At column 13, line 27, please delete "$(CP_2VX_2)$" and insert therefor, --$(Cp_2VX_2)$--.

At column 17, line 60, please delete "$(C_2H_5C_{54})_2VBr_2$," and insert therefor, --$(C_2H_5C_5H_4)_2VBr_2$,--.

At column 18, line 8-9, after "$VBr_2$" please delete

"$[1,3-(n-C_4H_9)_2C_5H_3]\,_2VBr_2, [1,3-(t-C_4H_9)_2C_5H_3]\,_2VI_2$," and insert therefor, --$[1,3-(n-C_4H_9)\,_2C_5H_3]\,VI_2, [1,3-(n-C_4H_9)\,_2C_5H_3]\,_2VF_2, [1,3-(t-C_4H_9)\,_2C_5H_3]\,_2VCl_2\,[1,3-(t-C_4H_9)\,_2C_5H_3]\,_2VBr_2, [1,3-(t-C_4H_9)\,_2C_5H_3]\,_2VI_2$,--.

At column 18, line 40, please delete "$[2-(CH_3)-4-C_6H_5Ind)]_2VF_2$" and insert therefor, --$(2-CH_3-4-C_6H_5Ind)_2\,VF_2$--.

At column 18, line 41, please delete

"$4-C_6H_5Ind)]\,_2VCI_2, (2-CH_3-4-C_6H_5Ind)\,_2VBr_2, (2-CH_3$" and insert therefor, --$4-C_6H_5Ind)\,_2VCl_2, (2-CH_3-4-C_6H_5Ind)\,_2VBr_2, (2-CH_3$--.

At column 19, line 3, please delete "$VCI_2$," and insert therefor, --$VCl_2$,--

UNITED STATES PATENT AND TRADEMARK OFFICE
CERTIFICATE OF CORRECTION

PATENT NO. : 6,849,753 B2
APPLICATION NO. : 10/298624
DATED : February 1, 2005
INVENTOR(S) : Tadanao Kohara It is certified that error appears in the above-identified patent and that said Letters Patent is hereby corrected as shown below:

At column 19, line 6, please delete "$2,4,8\text{-}(CH_3)_3Azu)_2Br_2$," and insert therefor, --$2,4,8\text{-}(CH_3)_3Azu)_2VBr_2$--

Signed and Sealed this

Fourth Day of December, 2007

JON W. DUDAS
*Director of the United States Patent and Trademark Office*